United States Patent [19]

Christensen et al.

[11] Patent Number: 4,783,453

[45] Date of Patent: Nov. 8, 1988

[54] 2-AZA-SUBSTITUTED 1-CARBADETHIAPEN-2-EM-3-CARBOXYLIC ACIDS

[75] Inventors: Burton G. Christensen, Cliffside Park; Ronald W. Ratcliffe, Matawan; John C. Chabala, Westfield, all of N.J.

[73] Assignee: Merck & Co., Inc., Rahway, N.J.

[21] Appl. No.: 97,348

[22] Filed: Sep. 8, 1987

Related U.S. Application Data

[63] Continuation of Ser. No. 743,199, Jun. 10, 1985, abandoned.

[51] Int. Cl.[4] .................... C07D 487/04; A61K 31/40
[52] U.S. Cl. .................................... 514/210; 540/302
[58] Field of Search ........................ 540/302; 514/210

[56] References Cited

U.S. PATENT DOCUMENTS

| | | | |
|---|---|---|---|
| 3,950,357 | 4/1976 | Kahan | 540/302 |
| 4,194,047 | 4/1980 | Christensen | 546/272 |
| 4,206,219 | 6/1980 | Christensen | 514/210 |
| 4,217,453 | 8/1980 | Christensen | 544/373 |
| 4,218,462 | 8/1980 | Christensen | 514/210 |
| 4,232,036 | 11/1980 | Christensen | 514/210 |
| 4,260,627 | 4/1981 | Christensen | 514/210 |
| 4,262,009 | 4/1981 | Christensen | 514/210 |
| 4,290,947 | 9/1981 | Christensen | 540/302 |
| 4,309,346 | 1/1982 | Christensen | 540/302 |
| 4,310,538 | 1/1982 | Christensen | 514/210 |
| 4,312,871 | 1/1982 | Christensen | 514/210 |
| 4,318,912 | 3/1982 | Christensen | 514/210 |
| 4,383,946 | 5/1983 | Christensen | 540/302 |
| 4,424,230 | 1/1984 | Christensen | 514/210 |
| 4,465,632 | 8/1984 | Christensen | 514/210 |
| 4,565,808 | 1/1986 | Christensen | 514/80 |

FOREIGN PATENT DOCUMENTS

| | | |
|---|---|---|
| 0058317 | 1/1982 | European Pat. Off. . |
| 0134301 | 9/1983 | European Pat. Off. . |
| 7973 | 2/1984 | European Pat. Off. . |
| 59-212493 | 12/1984 | Japan . |

OTHER PUBLICATIONS

Tetrahedron Letters, vol. 26, No. 44 (1985) pp. 5407–5410.
J. Org. Chem., 1985, 50, pp. 1996–1998.
Heterocycles, vol. 22, No. 11, pp. 2487–2490.
Advances in Heterocyclic Chemistry by P. K. Kadaba, vol. 37, pp. 217–350 (1984).
Heterocycles, vol. 21, No. 1, pp. 29–40 (1984).

Primary Examiner—Robert Gerstl
Attorney, Agent, or Firm—Robert J. North; Hesna J. Pfeiffer

[57] ABSTRACT

Disclosed are 2-aza-substituted 1-carbadethiapen-2-em-3-carboxylic acids I, where the generic 2-aza group includes azido, acylamino, amino, alkylamino, dialkylamino, triazolyl, triazolinyl, aziridinyl, and their pharmaceutically acceptable salt, ester, anhydride and amide derivatives which are useful as antibiotics. Also disclosed are processes for the preparation of I from the known, appropriately substituted bicyclic keto ester II via the 2-azido central intermediate III:

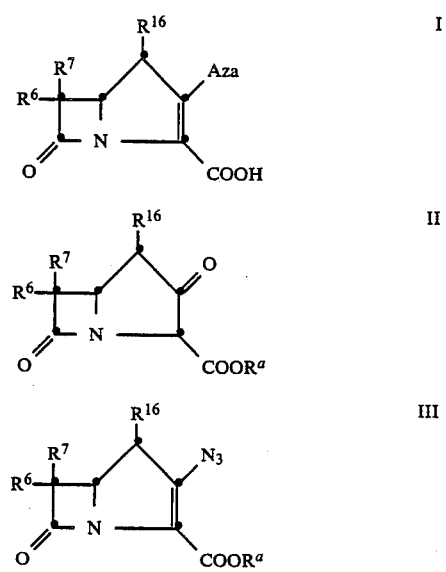

wherein $R^{16}$ is H or $CH_3$, preferably beta-methyl; $R^6$, and $R^7$ are independently hydrogen, linear, branched or cyclic $C_1$–$C_5$ alkyl, which can be substituted with fluoro, hydroxy, protected hydroxy, sulfoxy, amino, protected amino, wherein $R^6$ and $R^7$ taken together can also be $C_2$–$C_4$ alkylidene, similarly substituted; with the proviso that both $R^6$ and $R^7$ are not unsubstituted alkyl, $R^1$ and $R^2$ are, inter alia, hydrogen, alkyl, acyl, and can be joined to form a ring comprising 3 to 7 atoms; $R^a$ is hydrogen, a salt cation, a removable protecting group, or a pharmaceutically acceptable ester moiety.

Also disclosed are processes for the preparation of such compounds; pharmaceutical compositions comprising such compounds; and methods of treatment comprising administering such compounds and compositions when an antibiotic effect is indicated.

8 Claims, No Drawings

2-AZA-SUBSTITUTED 1-CARBADETHIAPEN-2-EM-3-CARBOXYLIC ACIDS

This is a continuation of application Ser. No. 743,199, filed June 10, 1985 now abandoned.

BACKGROUND OF THE INVENTION

The present invention relates to carbapenem antibiotics having a 2-aza substituent including azido, acylamino, amino, alkyl- and dialkylamino, triazolyl, triazolinyl, aziridinyl, and their pharmaceutically acceptable salt, ester, amide and anhydride derivatives.

Carbapenem antibiotics are known in the art, principally due to the discovery of thienamycin, which exhibits a therapeutically exciting and attractive broad spectrum of antibiotic activity, being of the formula:

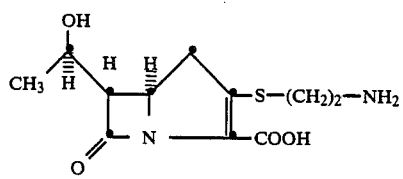

which is disclosed and claimed in U.S. Pat. No. 3,950,357.

The N-formimidoyl derivative of thienamycin, which is crystalline and a commercially more viable form of thienamycin, also exhibits a desirable broad spectrum of antibiotic activity and is disclosed and claimed in U.S. Pat. No. 4,194,047, which also discloses a method for its synthesis from thienamycin.

Despite the surprising and extraordinary broad spectrum antibiotic activity of thienamycin and its derivatives, there still exists a continuing need for new and more effective antibiotics. For unfortunately, there is not static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues and this is particularly true in the carbapenem family of compounds.

For example, U.S. Pat. No. 4,424,230 to B. G. Christensen et al. (which issued Jan. 3, 1984 and is assigned to Merck & Co. Inc.) discloses 6-(1'-hydroxyethyl)-3-substituted amino-1-azabicyclo[3.2.0]-hept-2-en-7-one carboxylic acids of the following formula:

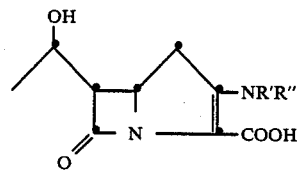

wherein R' and R" are independently selected from H, substituted and unsubstituted alkyl and aralkyl groups, or together form a substituted or unsubstituted cyclic group.

Further, U.S. Pat. No. 4,217,453 to B. G. Christensen et al. (which issued Aug. 12, 1980, and is assigned to Merck & Co. Inc.) discloses 6-amido-3-substituted-amino-1-azabicyclo[3.2.0]hept-2-en-7-one-2-carboxylic acid of the formula:

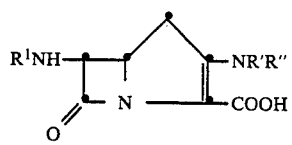

wherein $R^1$ is hydrogen or acyl; and R' and R" are independently selected from the group consisting of hydrogen, substituted or unsubstituted; alkyl and aralkyl, or together form a substituted or unsubstituted cyclic group.

The reference *Heterocycles*, Volume 22, No. 11, Pages 2487–2490, describes the reaction of C(3)-azido cephem with Grignard reagents to form triazines and with a variety of electron rich dipolarophiles to give C(3)-substituted amidines, imidates, iminolactones and aziridines. Carbapenems, however, are not specifically mentioned.

Thus, it is an object of the present invention to provide a novel class of antibiotics which are useful in animal and human therapy and in inanimate systems. These antibiotics are believed to be active against a broad range of pathogens which representatively include both Gram positive bacteria such as *S. aureus, Strep. pyogenes,* and *B. subtilis,* and Gram negative bacteria such as *E. coli,* Pseudomonas, *Proteus morganii,* Serratia, and Klebsiella. Further objects of this invention are to provide chemical processes for the preparation of such antibiotics and their nontoxic, pharmaceutically acceptable salts and derivatives; pharmaceutical compositions comprising such antibiotics; and to provide methods of treatment comprising administering such antibiotics and compositions when an antibiotic effect is indicated.

SUMMARY OF THE INVENTION

In accordance with this invention there is provided a compound having the structure:

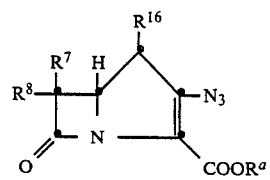

wherein $R^a$ is hydrogen, a salt cation, an ester blocking group or a pharmaceutically acceptable ester group; wherein $R^6$ and $R^7$ are selected from hydrogen, linear, branched or cyclic $C_1$-$C_5$ alkyl, which can be substituted with fluoro, hydroxy, protected hydroxy, sulfoxy, amino, protected amino; wherein $R^6$ and $R^7$ taken together can also be $C_2$-$C_4$-alkylidene, optionally substituted by the above substituents; with the proviso that both $R^6$ and $R^7$ are not unsubstituted alkyl; and wherein $R^{16}$ is independently hydrogen or methyl.

Also provided is a compound of the formula:

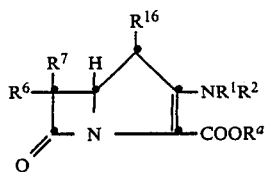

wherein $R^a$ is hydrogen, a salt cation, an ester blocking group or a pharmaceutically acceptable ester group; and $R^7$ and $R^6$ are selected from hydrogen, linear, branched or cyclic $C_1-C_5$ alkyl, which can be substituted with fluoro, hydroxy, protected hydroxy, sulfoxy, amino, protected amino, wherein $R^6$ and $R^7$ taken together can also be $C_2-C_4$ alkylidene, optionally substituted by the above substituents, with the proviso that both $R^6$ and $R^7$ are not unsubstituted alkyl; $R^{16}$ is H or methyl; wherein $R^1$ is selected from the group consisting of: hydrogen; substituted and unsubstituted non-acyl hydrocarbyl and $R^2$ is acyl. By the term "non-acyl hydrocarbyl" is meant a hydrocarbyl group attached directly to the amino nitrogen by a non-acyl linkage. The term "hydrocarbyl" is meant to include: alkyl, alkenyl, and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; aryl such as phenyl; aralkyl, aralkenyl, and aralkynyl wherein the aryl moiety is phenyl and the aliphatic portion has 1–6 carbon atoms; heteroaryl, heteroaralkyl, heterocyclyl, and heterocyclylalkyl; wherein the heteroatom or atoms are selected from the group consisting of 1–4 oxygen, nitrogen or sulfur atoms and the alkyl moieties associated with said heterocyclic moieties have 1–6 carbon atoms; wherein the substituent or substituents on $R^1$ are independently selected from carboxyl, sulfo, $C_1-C_6$ alkyl, $C_1-C_6$ alkoxy, ($C_1-C_6$ alkoxy)carbonyl, chloro, bromo, fluoro, hydroxy, cyano, nitro, amino, mono($C_1-C_4$ alkyl)amino, di($C_1-C_4$ alkyl)amino, $C_1-C_6$ alkylthio, $C_1-C_6$ alkylsulfinyl, $C_1-C_6$ alkylsulfonyl, carbamoyl which is optionally substituted on the N-atom with one or two $C_1-C_4$ alkyl, sulfamoyl, ($C_1-C_6$ alkyl)carbonyl, arylcarbonyl, or heteroarylcarbonyl. By the term "acyl" is meant wherein $R^2$ is chosen from the group consisting of:

$$-\overset{O}{\underset{\|}{C}}R^3, -\overset{O}{\underset{\|}{C}}OR^4, -\overset{O}{\underset{\|}{C}}SR^4, -\overset{O}{\underset{\|}{C}}NR^4R^5, -\overset{S}{\underset{\|}{C}}R^3, -\overset{S}{\underset{\|}{C}}OR^4,$$

$$-\overset{S}{\underset{\|}{C}}NR^4R^5, -\overset{O}{\underset{\|}{S}}R^3, -\overset{O}{\underset{\|}{\underset{O}{S}}}OR^4, -\overset{O}{\underset{\|}{\underset{O}{S}}}NR^4R^5, -\overset{O}{\underset{\underset{OR^5}{|}}{P}}-OR^4,$$

$$\overset{O}{\underset{\|}{P}}(NR^4R^5)_2, \overset{S}{\underset{\underset{OR^5}{|}}{P}}-OR^4, \overset{S}{\underset{\underset{SR^5}{|}}{P}}-SR^4,$$

wherein $R^3$ is selected from the group consisting of: hydrogen; substituted and unsubstituted: alkyl, alkenyl, and alkynyl having from 1–10 carbon atoms; cycloalkyl, cycloalkylalkyl, and alkylcycloalkyl having 3–6 carbon atoms in the cycloalkyl ring and 1–6 carbon atoms in the alkyl moieties; aryl; aralkyl, aralkenyl, and aralkynyl wherein the aryl moiety is phenyl and the aliphatic portion has 1–6 carbon atoms; heteroaryl, heteroaralkyl, heterocyclyl, and heterocyclylalkyl; wherein the heteroatom or atoms are selected from the group consisting of 1–4 oxygen, nitrogen or sulfur atoms and the alkyl moieties associated with said heterocyclic moieties have 1–6 carbon atoms and wherein the heteroaryl group can be optionally quaternized on a ring nitrogen atom with a $C_1-C_4$ alkyl group; wherein the substituents or substituents on $R^3$ are independently selected from one or more of carboxyl, $C_1-C_6$ alkyl, $C_1-C_6$ alkoxy, ($C_1-C_6$ alkoxy)carbonyl, bromo, chloro, fluoro, azido, hydroxyl, sulfo, cyano, nitro, amino, mono($C_1-C_4$alkyl)amino, di($C_1-C_4$ alkyl)amino, tri($C_1-C_4$ alkyl)ammonium, $C_1-C_6$ alkylthio, $C_1-C_6$ alkylsulfinyl, $C_1-C_6$ alkylsulfonyl, carbamoyl which is optionally substituted on the N-atom with one or two $C_1-C_4$ alkyl, sulfamoyl, ($C_1-C_6$ alkyl)carbonyl, arylcarbonyl, heteroarylcarbonyl, ($C_1-C_6$ alkyl)carbonyloxy, ($C_1-C_6$ alkyl)carbonylamino, guanidino optionally substituted on one or more of the N-atoms with $C_1-C_4$ alkyl, and carbamimidoyl optionally substituted on one or two of the N-atoms with $C_1-C_4$ alkyl; and wherein $R^4$ and $R^5$ are independently selected from the group consisting of: hydrogen; substituted and unsubstituted: alkyl having from 1–10 carbon atoms; cycloalkyl, cycloalkylalkyl, and alkylcycloalkyl having 3–6 carbon atoms in the cycloalkyl ring and 1–6 carbon atoms in the alkyl moieties; aryl such as phenyl; aralkyl wherein the aliphatic portion has 1–6 carbon atoms; heteroaryl, heteroaralkyl, heterocyclyl, wherein the heteroatom or atoms are selected from the group consisting of 1–4 oxygen, nitrogen or sulfur moieties and the aliphatic portion has 1–6 carbon atoms and wherein the heteroaryl group can be optionally quaternized on a ring nitrogen atom with a $C_1-C_4$ alkyl group; wherein the substituent or substituents on $R^4$ and $R^5$ are independently selected from one or more of carboxyl, hydroxyl, amino, mono($C_1-C_4$ alkyl)amino, di($C_1-C_4$ alkyl)amino, tri($C_1-C_4$ alkyl)ammonium, $C_1-C_6$ alkoxy, $C_1-C_6$ alkylthio, $C_1-C_6$ alkylsulfinyl, $C_1-C_6$ alkylsulfonyl, cyano, carbamoyl which is optionally substituted on nitrogen with one or two $C_1-C_4$ alkyl, sulfamoyl, or sulfo; wherein substituents $R^4$ and $R^5$ can be joined together to form, along with the atoms to which they are attached, a 5–7 membered ring, which can be optionally substituted by one or more of the substituents named above and can be optionally interrupted by a hetero group such as oxygen, sulfur, amino, or mono($C_1-C_4$ alkyl)amino. $R^1$ and $R^2$ can also be linked together with the nitrogen atom to which they are attached to form a 5–7 membered heterocyclic ring, which can be optionally substituted with substituents defined above for $R^1$ and $R^2$.

In addition there is provided a compound of the formula:

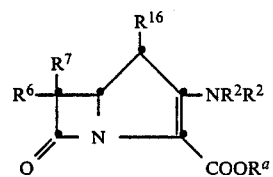

wherein $R^7$ and $R^6$ are selected from hydrogen, linear, branched or cyclic $C_1-C_5$ alkyl, which can be substituted with fluoro, hydroxy, protected hydroxy, sulfoxy, amino, protected amino, wherein $R^6$ and $R^7$ taken together can also be $C_2-C_4$ alkylidene, optionally substituted by the above substituents, with the proviso that both $R^6$ and $R^7$ are not unsubstituted alkyl; $R^{16}$ is H or methyl, and each $R^2$ is independently acyl, wherein $R^a$ and "acyl" are as defined hereinabove.

Furthermore, there is provided a compound of the formula:

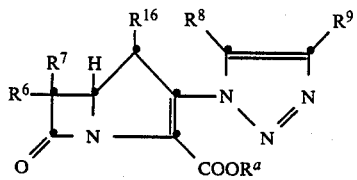

wherein $R^a$ is hydrogen, a salt cation, an ester blocking group or a pharmaceutically acceptable ester group; wherein $R^{16}$ is hydrogen or methyl; wherein $R^7$ and $R^6$ are selected from linear, branched or cyclic $C_1$-$C_5$ alkyl, which can be substituted with fluoro, hydroxy, protected hydroxy, sulfoxy, amino, protected amino, wherein $R^6$ and $R^7$ taken together can also be $C_2$-$C_4$ alkylidene, optionally substituted by the above substituents, with the proviso that both $R^6$ and $R^7$ are not unsubstituted alkyl, and $R^8$ and $R^9$ are independently chosen from H, alkyl, alkenyl, or alkynyl, optionally substituted with 1–3 substituents selected from halo, $OR^{11}$, $NR_2^{11}$, $COR^{11}$, $CONR_2^{11}$, $COR^{11}$, CN, $OCOR^{11}$, $NR^{11}C(X)R^{11}$, $N_3$, $R^{11}S$, $R^{10}SO$, $R^{10}SO_2$, and $OSO_2R^{10}$, wherein $R^{10}$=alkyl, aryl, or aralkyl, $R^{11}$=$R^{10}$ or H, and X=O, S, and $NR^{11}$; wherein $R^8$ and $R^9$ can also be chosen from aryl, aralkyl, 5- or 6-membered heteroaryl ring containing up to 4 atoms selected from O, S, or N and heteroaralkyl, which can be substituted with from 1 to 3 substituents selected from halo, alkyl, $CF_3$, $OR^{11}$, $NR_2^{11}$, $CO_2R^{11}$, $CONR_2^{11}$, $COR^{11}$, CN, $OCOR^{11}$, $NR^{11}C(X)R^{11}$, $R^{11}S$, $R^{10}SO$, or $R^{10}SO_2$; and wherein $R^8$ and $R^9$ can also be independently chosen from $OR^{11}$, $NR_2^{11}$, $CO_2R^{11}$, $CONR_2^{11}$, $COR^{11}$, CN, $OCOR^{11}$, $NR^{11}C(X)R^{11}$, $R^{11}S$, $R^{10}SO$, or $R^{10}SO_2$; and wherein $R^8$ and $R^9$ can also be joined to form a heterocyclic ring of from 5 to 7 members which contain up to 2 heteroatoms selected from O, N, S, SO, or $SO_2$.

In addition there is provided a compound of the formula:

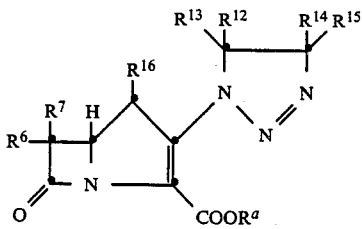

wherein $R^{16}$ is H or methyl; $R^7$ and $R^6$ are chosen from hydrogen, linear, branched or cyclic $C_1$-$C_5$ alkyl, which can be substituted with fluoro, hydroxy, protected hydroxy; sulfoxy, amino, protected amino, wherein $R^6$ and $R^7$ taken together can also be $C_2$-$C_4$ alkylidene, optionally substituted by the above substituents with the proviso that both $R^6$ and $R^7$ are not unsubstituted alkyl, and $R^a$ is hydrogen, a salt cation, an ester blocking group or a pharmaceutically acceptable ester group; wherein $R^{12}$, $R^{13}$, $R^{14}$, and $R^{15}$ are independently chosen from H, alkyl, alkenyl, and aralkynyl which can be mono- or di-substituted with halo, $OR^{11}$, $NR_2^{11}$, $CO_2R^{11}$, $CONR_2^{11}$, CN, $OCOR^{11}$, $COR^{10}$, $NR^{11}C(X)R^{11}$, $R^{11}S$, $R^{10}SO$, or $R^{10}SO_2$ wherein $R^{10}$ is alkyl, aryl, or aralkyl, $R^{11}$=$R^{10}$ or H, and X=O, S or NR"; wherein $R^{12}$, $R^{13}$, $R^{14}$, and $R^{15}$ can also be aryl, aralkyl, heteroaryl, or heteroaralkyl of 5- or 6-membered rings containing up to 4 atoms of O, N, or S, and can be substituted with up to 3 of halo, alkyl, $CF_3$, $OR^{11}$, $NR_2^{11}$, $CO_2R^{11}$, $CONR_2^{11}$, $COR^{11}$, CN, $OCOR^{11}$, $NR^{11}C(X)R^{11}$, $R^{11}S$, $R^{10}SO$, or $R^{10}SO_2$; and wherein $R^{12}$, $R^{13}$, $R^{14}$, and $R^{15}$, can also be up to 2 of $OR^{10}$, $NR_2^{10}$, $COR_2R^{11}$, $CONR_2^{10}$, CN, $COR^{11}$, $OCOR^{11}$, $NR^{11}C(X)R^{11}$, $R^{11}S$, $R^{10}SO$, or $R^{10}SO_2$; and further wherein $R^{12}$ and $R^{14}$ and/or $R^{13}$ and $R^{15}$ can be joined to form one or two rings each containing from 5 to 7 members containing up to 2 of O, N, S, SO, or $SO_2$, with the proviso that the total number of heteroatoms in both rings is not more than 2. The ring forming substituents $R^{12}$ and $R^{14}$ and/or $R^{13}$ and $R^{15}$ are cis oriented to each other.

Further provided is a compound of the formula:

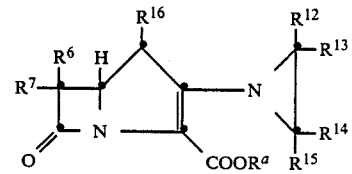

wherein $R^{16}$ is H or methyl; $R^7$ and $R^6$ are selected from hydrogen, linear, branched or cyclic $C_1$-$C_5$ alkyl, which can be substituted with fluoro, hydroxy, protected hydroxy; sulfoxy, amino, protected amino, wherein $R^6$ and $R^7$ taken together can also be $C_2$-$C_4$ alkylidene, optionally substituted by the above substituents, with the proviso that both $R^6$ and $R^7$ are not unsubstituted alkyl, $R^a$ is hydrogen, a salt cation, an ester blocking group or a pharmaceutically acceptable ester group; wherein $R^{12}$, $R^{13}$, $R^{14}$, and $R^{15}$ are independently chosen from: H, $C_1$-$C_4$ alkyl, which can be substituted with up to 2 groups selected from halo, $CO_2R^{11}$, $CONHR_2^{11}$, $COR^{11}$, $R^{10}SO$, and $R^{10}SO_2$, wherein $R^{10}$, is alkyl, aryl or aralkyl, $R^{11}$=$R^{10}$ or H and X=O, S or NR"; and further $R^{12}$, $R^{13}$, $R^{14}$, and $R^{15}$ can be aryl, aralkyl, heteroaryl, and heteroaralkyl of rings of 5 or 6 members containing from 0 to 4 atoms of O, N, or S, substituted with the substituents described above, further, $R^{12}$, $R^{13}$, $R^{14}$, and $R^{15}$ can be from 0 to 2 of $OCOR^{11}$, CN, $COR^{11}$, $CO_2R^{11}$, $CONR_2^{11}$, $R^{10}SO$, or $R^{10}SO_2$; and further, $R^{12}$ and $R^{14}$ and/or $R^{13}$ and $R^{15}$ be joined together in 1 to 2 rings of 5 to 7 members containing from 0 to 2 of O, N, S, SO, or $SO_2$ provided that the number of heteroatoms in both rings is no more than 4, and that a heterocyclic N atom occurs alpha to the bridge with the aziridine only in an acylated form. The ring forming substituents $R^{12}$ and $R^{14}$ and/or $R^{13}$ and $R^{15}$ are cis oriented to each other.

Also provided is a compound of the formula:

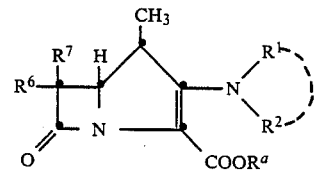

wherein $R^a$ is hydrogen, a salt cation, an ester blocking group, or pharmaceutically acceptable ester group, $R^7$ and $R^6$ are selected from hydrogen, linear, branched or cyclic, $C_1$–$C_5$ alkyl, which can be substituted with fluoro, hydroxy, protected hydroxy, sulfoxy, amino, protected amino, wherein $R^6$ and $R^7$ taken together can also be $C_2$–$C_4$ alkylidene, optionally substituted by the above substituents, with the proviso that both $R^6$ and $R^7$ are not unsubstituted alkyl, and $R^1$ and $R^2$ are independently selected from the group consisting of: hydrogen; substituted and unsubstituted non-acyl hydrocarbyl. By the term: "non-acyl hydrocarbyl" is meant alkyl, alkenyl, and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; aryl, aralkyl, aralkenyl, and aralkynyl wherein the aryl moiety is phenyl and the aliphatic portion has 1–6 carbon atoms; heteroaryl, heteroaralkyl, heterocyclyl, and heterocyclylalkyl; wherein the heteroatom or atoms are selected from the group consisting of 1–4 oxygen, nitrogen or sulfur atoms and the alkyl moieties associated with said heterocyclic moieties have 1–6 carbon atoms; wherein the substituent or substituents on $R^1$ and $R^2$ are independently selected from carboxyl, sulfo, $C_1$–$C_6$ alkyl, $C_1$–$C_6$ alkoxy, ($C_1$–$C_6$ alkoxy)carbonyl, chloro, bromo, fluoro, hydroxy, cyano, nitro, amino, mono($C_1$–$C_4$ alkyl)amino, di-($C_1$–$C_4$ alkyl)amino, $C_1$–$C_6$ alkylthio, $C_1$–$C_6$ alkylsulfinyl, $C_1$–$C_6$ alkylsulfonyl, carbamoyl which is optionally substituted on the N-atom with one or two $C_1$–$C_6$ alkyl, sulfamoyl, ($C_1$–$C_6$ alkyl)carbonyl, arylcarbonyl, or heteroarylcarbonyl.

In addition there is provided a process for making the compound of the formula IVA:

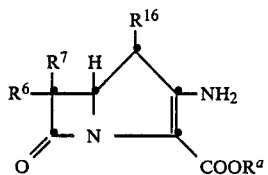

comprising the steps of:
(a) contacting the bicyclic ketoester

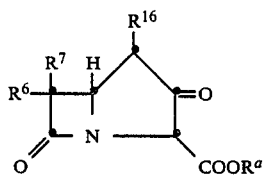

wherein $R^a$, $R^6$, $R^7$ and $R^{16}$ are as defined hereinabove, with an activating agent to form the 2-substituted carbapenem V:

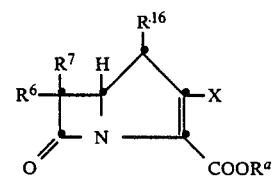

where X is a leaving group;
(b) contacting the above-formed carbapenem with an azide exchange reagent to form the azide compound III:

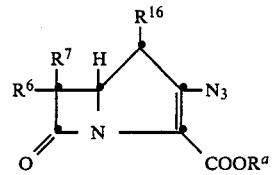

(c) reducing the above-formed azide compound by catalytic hydrogenation or chemical reduction to form the compound of formula (I); wherein $R^a$ is hydrogen, salt cation, an ester blocking group or a pharmaceutically acceptable ester group; $R^7$ and $R^6$ are selected from hydrogen, linear, branched or cyclic $C_1$–$C_5$ alkyl, which can be substituted with fluoro, hydroxy, protected hydroxy, sulfoxy, amino, protected amino, wherein $R^6$ and $R^7$ taken together can also be $C_2$–$C_4$ alkylidene, optionally substituted by the above substituents, with the proviso that both $R^6$ and $R^7$ are not unsubstituted alkyl; $R^{16}$ is hydrogen or methyl.

DESCRIPTION OF THE INVENTION AND PREFERRED EMBODIMENTS

As described above, this invention is directed to certain 2-aza-substituted 1-carbadethiapen-2-em-3-carboxylic acids of the general formula I, preferred compounds of Formula IB, and their pharmaceutical acceptable salt and ester derivatives which are useful as antibiotics

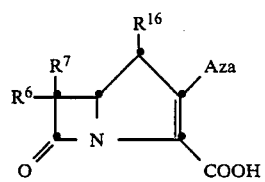

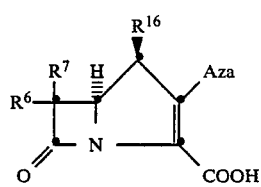

wherein $R^6$ and $R^7$ are independently hydrogen, linear, branched or cyclic $C_1$–$C_5$ alkyl, which can be substituted with fluoro, hydroxy, protected hydroxy, sulfoxy, amino, protected amino, or $R^6$ and $R^7$ taken together can also be $C_2$–$C_4$ alkylidene, similarly substituted; with the proviso that both $R^6$ and $R^7$ are not unsubstituted alkyl; and aza is —$N_3$ or —$NR^1R^2$ where $R^1$ and $R^2$ are inter alia, hydrogen, alkyl, acyl, and can be joined to form a ring comprising 3 to 7 atoms including triazolyl, triazolinyl, aziridinyl and $R^{16}$ is H or methyl, with the proviso that $R^{16}$ is methyl when $R^1$ and $R^2$ are H or alkyl. The values for $R^6$, $R^7$, $R^{16}$, $R^1$ and $R^2$ are defined in greater detail below.

Also described are processes for the preparation of the antibiotics of structure I via the 2-azido central intermediate III, from the known, appropriately substituted bicyclic ketoester II, described in European Patent No. 7973 and U.S. Pat. No. 4,310,538, both hereby incorporated by reference for that purpose,

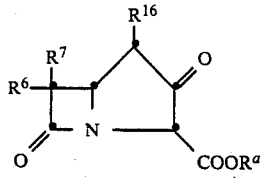

II

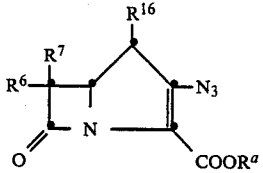

III wherein $R^a$ is hydrogen, a salt cation, a removable ester protecting group, or a pharmaceutically acceptable ester moiety.

Further disclosed are pharmaceutically acceptable carboxyl derivatives of I, including esters, anhydrides and amides, which are antibiotics and which may be represented by the following generic structure (IA):

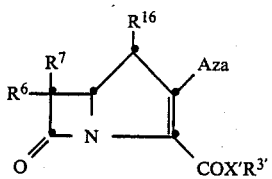

IA wherein X' is oxygen, sulphur or NR' (R'=H or lower alkyl having 1-6 carbon atoms); and $R^{3'}$ is, hydrogen, or, inter alia is representatively selected to provide the pharmaceutically acceptable salt, ester, anhydride ($R^{3'}$ is acyl), and amide moieties known in bicyclic β-lactam antibiotic art; $R^{3'}$ may also be a readily removable blocking group. The definition of $R^{3'}$ is given in greater detail below.

This invention also relates to pharmaceutical compositions comprising antibiotics of general formula I; and to methods of treatment comprising administering such compounds and compositions when an antibiotic effect is indicated.

More specifically the above-referred-to process of the present invention is characterized by the following reaction diagram:

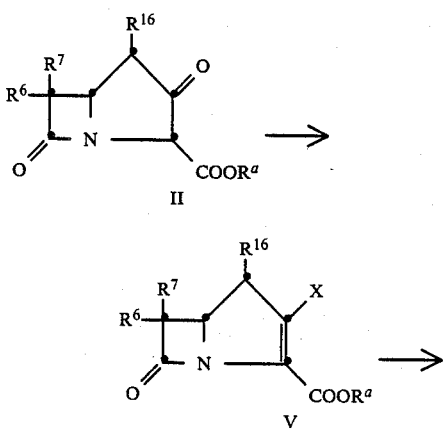

-continued

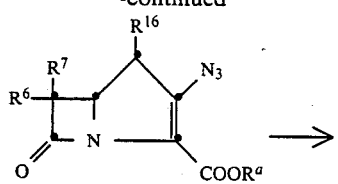

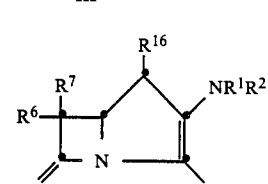

In words relative to the above diagram, the compounds of the present invention are essentially obtained by the above scheme, in the sequence II.→V.→III.→I. However, it is to be noted that the azido ester III is of central importance. The transformation III to IV is varied; its precise nature depends upon the identity of $R^1$ and $R^2$. Thus, the transformation III to IV will be categorizd below as a function of $R^1/R^2$. The transformation IV to I is, when indicated, the final deblocking step.

Starting material II is known, as is its activated form V; see, for example, U.S. Pat. No. 4,310,538, hereby incorporated by reference for this particular purpose.

Structure I, where $R^{16}=R^6=R^7=H$ is known and described for example, in U.S. Pat. No. 4,318,912, hereby incorporated by reference for that purpose. Where $R^6=$ 1-trimethylsilyloxyethyl and $R^{16}=R^7=H$, one preparation of the compound is disclosed in U.S. Pat. No. 4,318,912 by alkylating the carbapenem 6-position, with acetaldehyde in the presence of lithium diisopropylamide in THF. Suitable choice of alkylating agents, described in U.S. Pat. Nos. 4,309,346 and 4,383,946, leads to other values of $R^6$ and $R^7$. U.S. Pat. No. 4,290,947 also describes the 1-hydroxyethyl derivative and a method of making the preferred sterochemical derivative and the above four U.S. Patents are hereby incorporatad by reference for their description of methodology for making analogous alkylated analogues.

Within the scope of the compounds described herein, fluoro compounds, such as $CH_3CHF-$ and $FCH_2$, which are difficult to prepare by direct alkylation, can be prepared from the corresponding hydroxy compounds by treatment with DAST ™, diethylaminosulfur trifluoride, in an inert solvent, such as THF, at a temperature of −78° to 25° C. under an inert atmosphere for a period of about 1-2 hours.

Structure I, where $R^{16}$ is methyl, either alpha or beta, is described in the reference Heterocycles, Vol. 21, No. 1, pp. 29-49 (1984) hereby incorporated by reference for that purpose. Suitable alkylation reagents described above, will produce the corresponding 6-substituted-1-methyl ketoester derivatives.

In general the establishment of leaving group X (II to V) is accomplished by acylating the keto ester II with an acylating or activating agent RX such as p-toluenesulfonic acid anhydride, p-nitrophenylsulfonic acid anhydride, 2,4,6-triisopropylphenylsulfonic acid anhydride, methanesulfonic acid anhydride, toluenesulfonyl chloride, p-bromophenylsulfonyl chloride, diphenylchlorophosphate, trifluoromethanesulfonic anhydride, or the like; wherein X is the corresponding leaving group such as toluene sulfonyloxy, p-nitrophenylsulfonyloxy, methanesulfonyloxy, p-bromophenylsulfonyloxy, (diphenylphosphono)oxy, trifluoromethanesulfonyloxy and other leaving groups which are established by conventional procedures and which are known in the art. Typically, the above acylation to establish leaving groups X is conducted in a solvent such as methylene chloride ($CH_2Cl_2$), acetonitrile ($CH_3CN$), dimethylformamide (DMF), dimethylacetamide (DMAC), or tetrahydrofuran (THF), in the presence of an organic nitrogen base, such as diisopropylethylamine ($iPr_2NEt$), triethylamine ($Et_3N$), 4-dimethylaminopyridine (DMAP), imidazole, pyridine or the like, at a temperature of from $-20°$ to $40°$ C. for from 0.5 to 5 hours. The leaving group X of intermediate V can also be halogen. The halogen leaving group is established by treating II with a halogenating agent such as $\phi_3PCl_2$, $(\phi O)_3PCl_2$, $\phi_3PBr_2$, $(\phi O)_3PBr_2$, oxalyl chloride, $PBr_3$ or the like in a solvent such as $CH_2Cl_2$, $CH_3CN$, THF, or the like in the presence of a base such as diisopropylethylamine, triethylamine, or 4-dimethylaminopyridine or the like. [$\phi$=phenyl.]

The azide displacement transformation V to III is accomplished by treating V with an azide such as $KN_3$, $NaN_3$, $LiN_3$, tetramethylguanidinium azide, or the like, in a solvent such as THF, $CH_3CN$, $CH_2Cl_2$, DMF, $Et_2O$, DMAC, or the like, at a temperature of from $-40°$ to $50°$ C. for from 0.1 to 5 hours.

Alternatively, the bicyclic keto ester II can be converted into the vinyl azide III by using a reagent which both activates II and supplies an azide source For example, treating II with diphenylphosphoryl azide in a solvent such as $CH_2Cl_2$, THF, $CH_3CN$, or DMF in the presence of a base such as $Et_3N$, $iPr_2NEt$, or DMAP at a temperature of from $-20°$ C. to $60°$ C. for 0.5 to 4 hours provides III.

As mentioned, the azido ester III is the central intermediate leading to the final, antibiotic compounds I of the present invention. For example, reduction, e.g., catalytic hydrogenation, provides the 2-amino species IVA, wherein $R^1=R^2=H$:

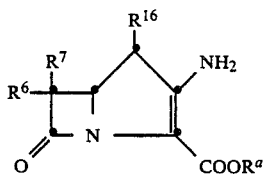

IVA

Such 2-amino species can be further derivatized; for example, N-alkylation, or N-acylation to provide the following embodiments of IV:

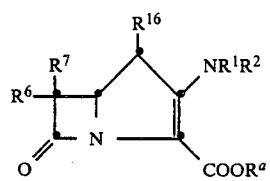

IV wherein $R^1$ and $R^2$ are independently chosen as described herein.

The azido ester also undergoes a wide variety of cycloaddition reactions to yield final products wherein $R^1$ and $R^2$ can be joined together:

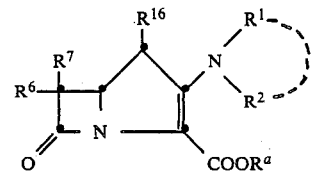

IVR

These and other reactions of the azido ester, which lead to the final antibiotics of the present invention, are described below. It should be noted that the transformation IV to I is a deblocking step and typically is accomplished by hydrogenolysis; for example, when $R^a$ is a substituted or unsubstituted benzyl group such as p-nitrobenzyl, IV in a solvent such as THF, dioxane, EtOH, nBuoH, EtOAc, $H_2O$, or the like, with or without added buffer or inorganic base in the presence of a catalyst such as Pd/C, $Pd(OH)_2/C$, $PtO_2$, or the like, is held at a temperature of from $0°$ to $40°$ C. under 1 to 4 atmospheres of hydrogen for 0.5 to 8 hours to provide I.

When the blocking ester $R^a$ is a substituted or unsubstituted allyl group, the deblocking is accomplished by a palladium (O) catalyzed transesterification process. For example, IV in a solvent such as EtOAc, $CH_2Cl_2$, THF, or $Et_2O$ is treated with a combination of triphenyl phosphine, tetrakistriphenylphosphine palladium (O), and 2-ethylhexanoic acid or its sodium or potassium salt. Use of either sodium or potassium 2-ethylhexanoate provides the corresponding salt of the product I, whereas 2-ethylhexanoic acid provides the free carboxylic acid.

Preparation of 2-amino species

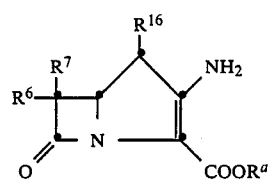

IVA $R^a$=H, protecting group, pharmaceutically acceptable ester moiety and $R^{16}=CH_3$ or H.

The reduction of azide III to amine IVA ($R^1=R^2=H$) can be accomplished by hydrogenating III under from 1 to 4 atmospheres hydrogen in the presence of a catalyst such as Lindlar's catalyst (Pd/$CaCO_3$/$Pb^{+2}$), Pd/$BaSo_4$, Pd/C, $Pd(OH)_2/C$, $PtO_2$, Pt/C, Raney nickel, or the like, in a solvent such as dioxane, tetrahydrofuran, diethyl ether, lower alkanols (1 to 4 carbon atoms), or the like, at a temperature of from $-20°$ C. to $40°$ C. for 0.1 to 4 hours to provide IV ($R^1=R^2=H$). Under vigorous hydrogenating conditions and when $R^a$ is a blocking group which can be removed by catalytic hydrogenation, the corresponding amino acid IV ($R^1=R^2=R^a=H$) is obtained. For example, hydrogenation of III when $R^a$ is p-nitrobenzyl at 3–5 atmospheres in a solvent system such as n-BuOH-EtOAc-$H_2O$-pH 7 buffer in the presence of 20% $Pd(OH))_2/C$ provides the amino acid IV ($R^1=R^2=R^a=H$).

Reduction of azide III to amino IVA ($R^1=R^2=H$) can also be accomplished non-catalytically by chemical reduction. Treatment of III with hydrogen sulfide, 1,3-propanedithiol, or thioglycolic acid in the presence of a base such as triethylamine, piperidine, or pyridine in a solvent such as ethanol, methanol, chloroform, or water at temperature of from 0° to 60° C. affords the amine IV ($R^1=R^2=H$). The amino derivative can also be prepared by treating III with triphenylphosphine followed by acidic hydrolysis of the phosphinimino intermediate or by treating III with a hydride reducing agent such as lithium aluminum hydride in $Et_2O$ or THF.

Preparation of 2-N-alkyl Species and 2-N-acyl Species

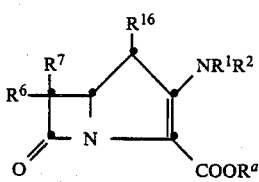

IV

Compounds of structure IV ($R^1=H$ and $R^2=$alkyl, alkenyl, alkynyl, aryl, aralkyl, heteroaryl or heteroaralkyl as described herein) are prepared by N-alkylation of IVA as the unsubstituted primary amine ($R^1=R^2=H$). There is no undue criticality in the process and any of a variety of well-known N-alkylation procedures may be employed. The identity of the N-alkylating agent is a matter of choice within the limits set by the definition of $R^2$. The N-alkylation may be conducted in any of a variety of solvent systems which are inert or substantially inert to the desired course of reaction. Suitable solvents include polar solvents wuch as water, lower alkanols such as ethanol, dioxane, tetrahydrofuran (THF), acetonitrile, hexamethylphosphoramide (HMPA), dimethylformamide (DMF) and the like and mixtures (particularly aqueous mixtures) of the above; and non-polar solvents such as benzene and halohydrocarbons such as methylene chloride, chloroform and the like. Typically the reaction is conducted at a temperature of from $-40°$ C. to 50° C. for from 15 minutes to 5 hours. Usually, the reaction is conducted in the presence of an acid acceptor such as propylene oxide, magnesium oxide, potassium carbonate and the like. The preferred N-alkylating agents include active halides, sulfate esters, and Michael addition reagents. The following reagents are representative of such alkylating agents: methyl iodide, allyl bromide, bromo acetone, phenacyl bromide, benzyl bromide, ethylchloroacetate, propargyl bromide, 2-bromoethylethylether, dimethyl sulfate, ethyl fluorosulphonate, methylfluorosulphonate, chloromethylthiocyanate, chloroethylmethylsulfide, bromoethylcyclopropane, 2,4-dinitrofluorobenzene, 2-chloromethylpyridine, acrylonitrile, methyl methacrylate, nitroethylene and the like.

The compounds IV wherein $R^1$ and $R^2$ are both chosen from alkyl, alkenyl, alkynyl, aryl, aralkyl, heteroaryl, heteroaralkyl and neither $R^1$ nor $R^2=H$ are prepared by N-alkylation of IV ($R^1=H$ and $R^2=$alkyl, alkenyl, alkenyl, aryl, aralkyl, heteroaryl, or heteroaralkyl) using the same conditions described for the preparation of IV ($R^1=H$, $R^2=$alkyl, alkenyl, alkynyl, aryl, aralkyl, heteroaryl or heteroaralkyl). The compounds IV wherein $R^{16}$ is $CH_3$, $R^1$ and $R^2$ are joined to form a ring from 3 to 7 atoms are prepared by performing the alkylation of IV ($R^1=R^2=H$) using a bifunctional alkylating agent $X-(CH_2)_n-Y$ wherein $n=2-5$ and X and/or Y are any of the variety of N-alkylating agents mentioned above.

Compounds of structure IV ($R^1=H$, alkyl, alkenyl, alkynyl, aryl, aralkyl, heteroaryl, or heteroaralkyl and $R^2=$acyl) and $R^{16}$ is H or $CH_3$, are prepared by N-acylation of IV ($R^1=R^2=H$ or $R^1=$alkyl, alkenyl, alkynyl, aryl, aralkyl, heteroaryl, or heteroaralkyl and $R^2=H$). There is no undue criticality in the process and any of a variety of well known N-acylation procedures may be employed. The identity of the N-acylating agent is a matter of choice within the limits set by the definition of $R^2$. The N-acylation may be conducted in any of a variety of solvent systems which are inert or substantially inert to the desired course of reaction. Suitable solvents include polar solvents such as tetrahydrofuran (THF), dioxane, acetonitrile, dimethylformamide (DMF), hexamethylphosphoramide, lower alkanols such as ethanol, water and the like and mixtures (particularly aqueous mixtures) of the above; and non-polar solvents such as benzene, ethyl ether, and halohydrocarbons such as methylene chloride, chloroform, and the like. Typically the reaction is conducted at a temperature of from $-40°$ C. to 50° C. for from 15 minutes to 20 hours. Usually the reaction is conducted in the presence of a base or acid acceptor such as propylene oxide, magnesium oxide, potassium carbonate, pyridine, 4-dimethylaminopyridine, triethylamine, or N,N-diisopropylethylamine and the like. The preferred N-acylating agents include acid halides, acid anhydrides, mixed acid anhydrides, active esters, thiolesters and the like. The following are representative of such acylating agents: acetyl chloride, acetic anhydride, methyl isocyanate, N,N-dimethylcarbamoyl chloride, methyl chloroformate, dimethyl chlorophosphate, methanesulfonyl chloride and the like. Alternatively, the acylating agent can be formed and reacted in situ from the corresponding acid and any of a number of known coupling reagents such as dicyclohexylcarbodiimide, diphenyl azidophosphate, 1-ethoxycarbonyl-2-ethoxydihydroquinoline and the like.

Compounds of structure IV wherein $R^1$ is an alkyl group linked to an acyl group $R^2$ by a covalent bond or wherein both $R^1$ and $R^2$ are acyl groups linked by a covalent bond to form an N-containing ring comprised of 5-6 atoms are prepared by reacting the amino intermediate IV ($R^1=R^2=H$) with a bifunctional agent containing an N-alkylating group and an N-acylating group or with a bifunctional agent containing two N-acylating groups. The reaction can be conducted using the conditions previously described for preparing monoalkylated and/or monoacylated products. The following are representative of such bifunctional reagents: N-carbethoxyphthalimide, maleic anhydride, 3-bromopropionyl chloride, succinyl chloride and the like.

Preparation of N-cycloaddition Products

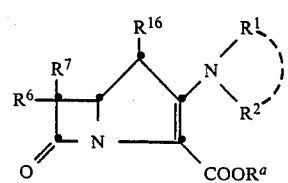

IVR

The central azide intermediate III also undergoes cycloaddition reactions with unsaturated compounds to provide a variety of products IVR wherein $R^1$ and $R^2$ are linked to form a ring.

1. Azide III reacts with alkynes VI to provide 1H-1,2,3-triazoles VII.

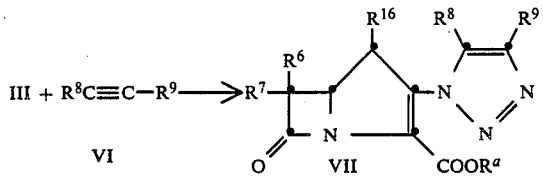

Substituents $R^8$ and $R^9$ are chosen inter alia from H, alkyl, aryl, aralkyl, heteroaryl, halo, $R^{10}O$, $R_2^{10}N$, $CO_2R^{11}$, $CONR''_2$, CN, $COR^{11}$, $OCOR^{11}$, $NR^{11}COR^{11}$, $R^{10}S$, $R^{10}SO$, and $R^{10}SO_2$, wherein $R^{10}$ is alkyl, aryl, or aralkyl and $R^{11}$ is H or chosen from $R^{10}$. $R^8$ and $R^9$ may also be joined to form a ring of from 5 to 7 atoms, containing up to 2 atoms of any combination of O, N, S, SO, or $SO_2$. The reaction may be performed neat or in solution in diethyl ether, tetrahydrofuran, dichloromethane, chloroform, dimethylsulfoxide, N,N-dimethylformamide, ethyl acetate, acetone, acetonitrile, toluene, ethanol, or the like, at temperatures of from $-40°$ to $100°$ for 10 minutes to two weeks. The regiochemistry and rate of addition is influenced by the nature of the substituents $R^8$ and $R^9$. Generally, polar electron donating substituents such as $OR^{10}$ and $NR_2^{10}$ enhance the rate of cycloaddition and provide products wherein the electron donating substituent is found predominantly in the 5-position of the product 1H-1,2,3-triazole. Polar electron withdrawing substituents such as $CO_2R^{11}$ and $SO_2R^{10}$ also enhance the rate of cycloaddition, but provide products wherein the electron withdrawing group is predominantly in the 4-position of the product 1H-1,2,3-triazole. Alkynes wherein $R^8$ and $R^9$ are nonpolar, such as alkyl and aralkyl, react at slower rates to form more nearly equal mixtures of isomeric 1H-1,2,3-triazoles.

2. Azide III also reacts with alkenes VII to provide $(\Delta^2)$-1,2,3-triazolines VIII.

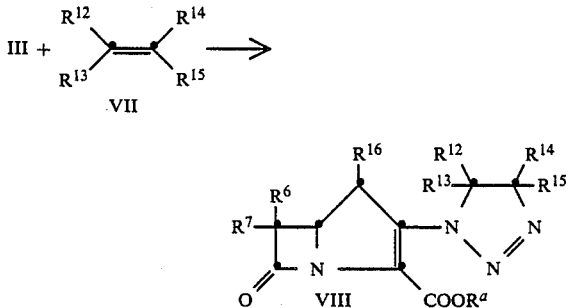

Substituents $R^{12}$, $R^{13}$, $R^{14}$, and $R^{15}$ are chosen from 1 to 4 of H, alkyl, aryl, aralkyl, heteroaryl, or halo, or 1 or 2 of $OR^{10}$, $OCOR^{11}$, $NR_2^{10}$, $NR^{11}COR^{11}$, $CO_2R^{11}$, $COR^{11}$, $CONR_2^{11}$, CN, $R^{10}S$, $R^{10}SO$, or $R^{10}SO_2$ wherein $R^{10}$ and $R^{11}$ are defined as in Part 1 above. $R^{12}$ and $R^{14}$ or $R^{13}$ and $R^{15}$ may be joined to form a ring containing from 5 to 7 atoms, up to 2 member of which may be O, N, S, SO or $SO_2$. The reaction may be performed neat or in solution in diethyl ether, tetrahydrofuran, dichloromethane, chloroform, dimethyl sulfoxide, N,N-dimethylformamide, ethyl acetate, acetone, acetonitrile, toluene, ethanol, or the like, at temperatures of from $-40°$ to $100°$ for 10 minutes to 2 weeks. Polarizing substituents enhance the rate of reaction. Electron donating substituents such as $OR^{10}$ and $NR_2^{10}$ provide products wherein the electron donating substituent is found predominantly in the 5-position of the $(\Delta^2)$-1,2,3-triazoline. Electron withdrawing substituents such as $CO_2R^{11}$ and $SO_2R^{10}$ provide products wherein the electron withdrawing substituent is found predominantly in the 4-position of the $(\Delta^2)$-1,2,3-triazoline I. The stereochemistry of olefin VII is generally retained in $(\Delta^2)$-1,2,3-triazoline.

3. The $(\Delta^2)$-1,2,3-triazolines may be converted to aziridines IX and/or imines X by thermolysis or photolysis. The aziridine and/oriimine may also be prepared directly from azide III without isolation of intermediate $(\Delta^2)$-1,2,3-triazoline if desired. Sometimes the rate of decomposition of the $\Delta^2$-1,2,3-triazoline to the aziridine and/or imine is faster than its rate of formation, thereby precluding isolation of the triazoline intermediate.

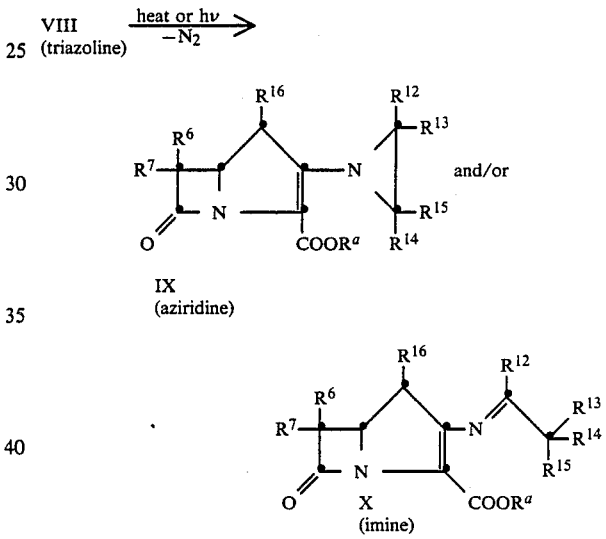

The thermolytic conversion of $(\Delta^2)$-1,2,3-triazolines VIII to aziridines IX and/or imine X or azides III to aziridines IX and/or imines X is performed neat or in solution in diethyl ether, tetrahydrofuran, dichloromethane, chloroform, dimethyl sulfoxide, N,N-dimethylformamide, ethyl acetate, acetonitrile, acetone, toluene, ethanol, or the like, at temperatures of from $-20°$ to $150°$ C. for from 10 min. to 24 hours. Alternatively, $(\Delta^2)$-1,2,3-triazoline is converted by ultraviolet irradiation to aziridine IX in solution in diethyl ether, tetrahydrofuran, dichloromethane, ethyl acetate, dimethyl sulfoxide, or the like, at temperatures of from $-80°$ to $25°$ C. for from 10 minutes to 12 hours.

The substituents on ring carbons C4 and C5 of the $\Delta^2$-1,2,3-triazoline VIII play an important role in directing product formation during tiazoline thermolysis. Imines X are usually formed when an electron denoting group such as $NR_2^{10}$ or $OR^{10}$ is present on C5, whereas electron withdrawing groups such as $CO_2R^{11}$ or CN on C4 lead mainly to aziridines IX with a marked retention of the original triazoline geometry. Alkyl and aryl groups at C4 or C5 usually lead to mixtures of aziridines and imines. These factors, as well as the conversion of certain $\Delta^2$-1,2,3-triazolines into 1H-1,2,3-triazoles (vide infra), have been reviewed by P. K. Kadaba in *Advances in Heterocyclic Chemistry*, Vol. 37, Edit. A. R. Katritzky, Academic Press (1984), pp. 217-350, hereby incorporated by reference for this particular purpose.

4. Appropriately substituted ($\Delta^2$)-1,2,3-triazolines react to eliminate the elements of $HR^{12}$, $HR^{13}$, $HR^{14}$, or $HR^{15}$, to provide 1H-1,2,3triazoles VII wherein the remaining substituents $R^{12}$, $R^{13}$, $R^{14}$, or $R^{15}$ are $R^8$ or $R^9$. Appropriately substituted ($\Delta^2$)-1,2,3-triazolines are those wherein $R^{12}$ or $R^{13}$ is $OR^{10}$, $NR_2^{10}$, $OCOR^{11}$, or $SR^{10}$ and either or both of $R^{14}$ and/or $R^{15}$ is H, or $R^{14}$ or $R^{15}$ is CN, $SO_2R^{10}$, Cl or F and either or both of $R^{12}$ and/or $R^{13}$ is H. The reaction may be performed neat or in solution in diethyl ether, tetrahydrofuran, dichloromethane, chloroform, dimethyl sulfoxide, N,N-dimethylformamide, ethyl acetate, acetonitrile, toluene, ethanol or the like, in the presence or absence of an inorganic or organic base such as $NaHCO_3$, $K_2CO_3$, $Na_2HPO_4$, $Et_3N$, $iPr_2NEt$, pyridine, 4-dimethylaminopyridine, or the like, at temperatures of from $-50°$ to $100°$ for 10 minutes to 2 weeks.

Definition of $R^6$ and $R^7$ and $R^{16}$

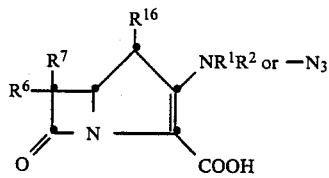

IV

The substituent $R^{16}$ is selected from H or $CH_3$. Preferably the substituent is methyl and most preferably in the beta-methyl configuration.

The substituents $R^7$ and $R^6$ are independently selected from the group: hydrogen, linear, branched or cyclic $C_1$-$C_5$ alkyl, which can be substituted with fluoro, sulfoxy, amino, protected amino, hydroxy and protected hydroxy, wherein $R^6$ and $R^7$ taken together can also be $C_2$-$C_4$alkylidene, optionally substituted by the same above-described substituents, with the proviso that both $R^6$ and $R^7$ are not unsubstituted alkyl.

Representative examples of $R^6$ and $R^7$ include but are not limited to: hydrogen, $CH_3CH_2-$, $(CH_3)_2CH-$, $HOCH_2-$, $CH_3CHOH-$, $CH_3CH(OR^p)-$, where $R^p$ is a known protecting group in the antibiotic carbapenem art including allyloxycarbonyl, p-nitrobenzyloxycarbonyl, tri-methylsilyl (TMS), t-butyl-dimethylsilyl (TBDMS) and the like, $(CH_3)_2COH-$, $FCH_2CHOH-$, $FCH_2-$, $F_2CH-$, $F_3C-$, $CH_3CHF-$, $CH_3CF_2-$, $(CH_3)_2CF-$, $CH_3CH(OSO_3H)-$, $CH_3CH(NH_2)-$, $CH_3CH(NHR^p)-$, and $(CH_2)_2C(OH)-$.

A preferred embodiment of the present invention comprises compounds of formula IV wherein $R^7$ is hydrogen, $R^{16}$ is hydrogen or methyl, and $R^6$ is hydrogen, $CH_3CH_2-$,

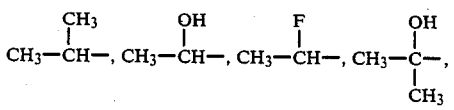

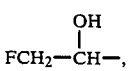

$CH_3CHF-$, $CH_3CF_2-$, $CH_3CHOSO_3H$, $(CH_2)_2COH-$, or $CH_3CHNH_2-$.

Among this subclass, the preferred compounds are those in which $R^7$ is H and $R^6$ is

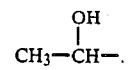

Another preferred embodiment comprises compounds of formula IV in which $R^{16}$ is hydrogen or methyl and $R^6$ and $R^7$ taken together form an alkylidene radical, e.g.

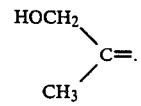

The compounds of the present invention contain several contiguous chiral centers. For example, the non-hydrogen $R^6$, $R^7$, and $R^{16}$ substituents may be in either the $\alpha$- or $\beta$-configurations, and it is intended that the present invention include the individual $\alpha$- and $\beta$-isomers, as well as mixtures thereof. The most preferred compounds wherein $R^7$ is hydrogen, $R^{16}$ is hydrogen or methyl, and $R^6$ is hydroxyethyl have the absolute stereochemistry shown below:

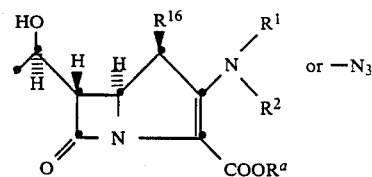

Preferred 2-aza compounds of the configuration:

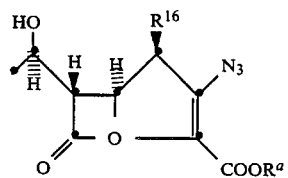

are as follows:

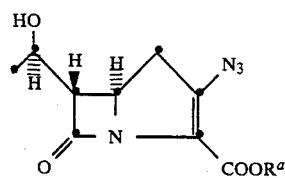

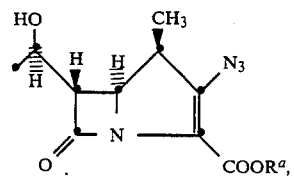

-continued

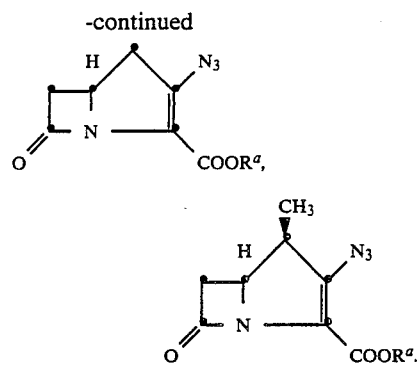

where $R^a$ is benzyl, p-nitrobenzyl, allyl, sodium, or potassium.

Definition of $R^1$, $R^2$ as Alkyl

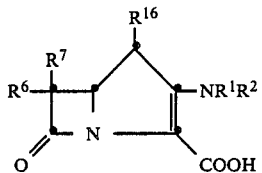
I

Where $R^{16}$ is $CH_3$, the substituents $R^1$ and $R^2$ are independently selected from the group consisting of: hydrogen; substituted and unsubstituted: alkyl, alkenyl, and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; aryl such as phenyl; aralkyl, aralkenyl, and aralkynyl wherein the aryl moiety is phenyl and the aliphatic portion has 1–6 carbon atoms; heteroaryl, heteroaralkyl, heterocyclyl, and heterocyclylalkyl; wherein the heteroatom or atoms are selected from the group consisting of 1–4 oxygen, nitrogen or sulfur atoms and the alkyl moieties associated with said heterocyclic moieties have 1–6 carbon atoms; wherein the substituent or substituents on $R^1$ and $R^2$ are independently selected from carboxyl, sulfo, $C_1$–$C_6$ alkyl, $C_1$–$C_6$ alkoxy, ($C_1$–$C_6$ alkoxy)carbonyl, chloro, bromo, fluoro, hydroxy, cyano, nitro, amino, mono($C_1$–$C_4$ alkyl)amino, di($C_1$–$C_4$ alkyl)amino, $C_1$–$C_6$ alkylthio, $C_1$–$C_6$ alkylsulfinyl, $C_1$–$C_6$ alkylsulfonyl, carbamoyl which is optionally substituted on the N-atom with one or two $C_1$–$C_4$ alkyl, sulfamoyl, ($C_1$–$C_6$ alkyl)carbonyl, arylcarbonyl, or heteroarylcarbonyl.

A preferred embodiment of this class comprises compounds of formula I wherein $R^1$ and $R^2$ are independently selected from hydrogen, $CH_3$, $CH_2CH_3$, $CH_2CH=CH_2$, $CH_2C_6H_5$, $CH_2$-pyridyl, $CH_2CH_2N(CH_3)_2$, $CH_2CH_2OH$, $CH_2CN$, $CH_2OCH_3$, $CH_2SCH_3$, or $CH_2CH_2CO_2H$.

Among this class, particularly preferred compounds are those in which $R^1$ is hydrogen and $R^2$ is $CH_3$ or $CH_2C_6H_5$ and both $R^1$ and $R^2$ are $CH_3$.

Definitions of $R^1$, $R^2$ as Acyl

1. Monoacylated species ($R^1$ is H, alkyl, alkenyl, alkynyl, aryl, aralkyl, or heteroaralkyl and $R^2$ is acyl) where $R^{16}$ is H or $CH_3$. The substituent $R^1$ is as previously defined for $R^1$, $R^2$ as alkyl and $R^2$ is chosen from the acyl group consisting of:

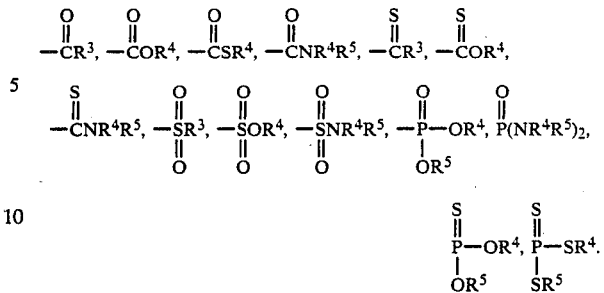

The substituent $R^3$ is selected from the group consisting of: hydrogen; substituted and unsubstituted: alkyl, alkenyl, and alkynyl having from 1–10 carbon atoms; cycloalkyl, cycloalkylalkyl, and alkylcycloalkyl having 3–6 carbon atoms in the cycloalkyl ring and 1–6 carbon atoms in the alkyl moieties; aryl such as phenyl; aralkyl, aralkenyl, and aralkynyl wherein the aryl moiety is phenyl and the aliphatic portion has 1–6 carbon atoms; heteroaryl, heteroaralkyl, heterocyclyl, and heterocyclylalkyl; wherein the heteroatom or atoms are selected from the group consisting of 1–4 oxygen, nitrogen or sulfur atoms and the alkyl moieties associated with said heterocyclic moieties have 1–6 carbon atoms; and wherein the heteroaryl group can be optionally quaternized on a ring nitrogen atom with a $C_1$–$C_4$ alkyl group; wherein the substituents or substituents on $R^3$ are independently selected from one or more of carboxyl, $C_1$–$C_6$ alkyl, $C_1$–$C_6$ alkoxy, ($C_1$–$C_6$ alkoxy)carbonyl, bromo, chloro, fluoro, azido, hydroxyl, sulfo, cyano, nitro, amino, mono($C_1$–$C_4$ alkyl)amino, di($C_1$–$C_4$ alkyl)amino, tri($C_1$–$C_4$ alkyl)ammonium, $C_1$–$C_6$ alkylthio, $C_1$–$C_6$ alkylsulfinyl, $C_1$–$C_6$ alkylsulfonyl, carbamoyl which is optionally substituted on the N-atom with one or two $C_1$–$C_4$ alkyl, sulfamoyl, ($C_1$–$C_6$ alkyl)carbonyl, arylcarbonyl, heteroarylcarbonyl, ($C_1$–$C_6$ alkyl)carbonyloxy, ($C_1$–$C_6$ alkyl)carbonylamino, guanidino optionally substituted on one or more of the N-atoms with $C_1$–$C_4$ alkyl, and carbamimidoyl optionally substituted on one or two of the N-atoms with $C_1$–$C_4$ alkyl.

The substituents $R^4$ and $R^5$ are independently selected from the group consisting of: hydrogen; substituted and unsubstituted: alkyl having from 1–10 carbon atoms; cycloalkyl, cycloalkylalkyl, and alkylcycloalkyl having 3–6 carbon atoms in the cycloalkyl ring and 1–6 carbon atoms in the alkyl moieties; aryl such as phenyl; aralkyl wherein the aliphatic portion has 1–6 carbon atoms; heteroaryl, heteroaralkyl, heterocyclyl, wherein the heteroatom or atoms are selected from the group consisting of 1–4 oxygen, nitrogen or sulfur moieties and the aliphatic portion has 1–6 carbon atoms; and wherein the heteroaryl group can be optionally quaternized on a ring nitrogen atom with a $C_1$–$C_4$ alkyl group; wherein the substituent or substituents on $R^4$ and $R^5$ are independently selected from one or more of carboxyl, hydroxyl, amino, mono($C_1$–$C_4$ alkyl)amino, di($C_1$–$C_4$ alkyl)amino, tri($C_1$–$C_4$ alkyl)ammonium, $C_1$–$C_6$ alkoxyl, $C_1$–$C_6$ alkylthio, $C_1$–$C_6$ alkylsulfinyl, $C_1$–$C_6$ alkylsulfonyl, cyano, carbamoyl which is optionally substituted on nitrogen with one or two $C_1$–$C_4$ alkyl, sulfamoyl, or sulfo. The substituents $R^4$ and $R^5$ may also be joined together to form, along with the atoms to which they are attached, a 5–7 membered ring. Such rings may be optionally substituted by one or more of the substituents named above and may be optionally interrupted by a hetero group such as oxygen, sulfur, amino, or mono($C_1$-$C_4$ alkyl)amino.

A preferred embodiment of this class comprises compounds of formula I wherein $R^1$ is hydrogen or $CH_3$ and $R^2$ is

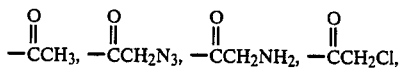

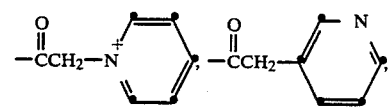

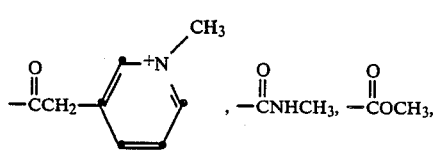

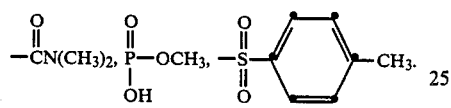

A particularly preferred embodiment of this class comprises compounds of formula I wherein $R^1$ is hydrogen and $R^2$ is

2. Cyclic mono- and diacylated species ($R^1$ is alkyl linked to $R^2$ is acyl or both $R^1$ and $R^2$ are acyl linked together). The substituents $R^1$ and $R^2$ are as previously defined for $R^1$, $R^2$ as alkyl and $R^1$, $R^2$ as acyl except that neither $R^1$ or $R^2$ can be hydrogen and one or both of $R^2$ and $R^2$ must be acyl, and $R^1$ and $R^2$ are linked by a covalent bond to form, together with the nitrogen atom to which they are attached, a 5-7 membered ring. The linking bond may emanate from any of the substituents $R^3$, $R^4$ or $R^5$ or may replace one or two of these substituents. The resulting 5-7 membered ring may be optionally substituted by one or more of the substituents previously defined for $R^1$, $R^2$ as acyl and may contain an additional fused aryl or heteroaryl ring.

A preferred embodiment of this class comprises compounds of formula I wherein the group

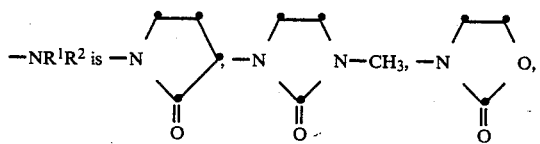

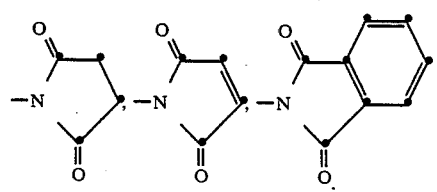

Definition of

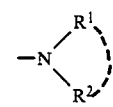

Moiety of Structure I

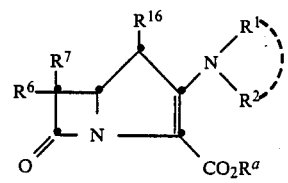

1. Triazoles

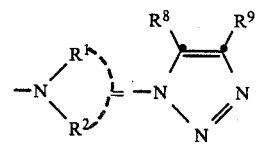

The substituents $R^8$ and $R^9$ are independently chosen from H, alkyl, alkenyl, or alkynyl, substituted with 0-3 of any of halo, $OR^{11}$, $NR_2^{11}$, $CO_2R^{11}$, $CONR_2^{11}$, $COR^{11}$, CN, $OCOR^{11}$, $NR^{11}C(X)R^{11}$, $N_3$, $R^{11}S$, $R^{10}SO_2$, and $OSO_2R^{10}$ wherein $R^{10}$=alkyl, aryl, or aralkyl, $R^{11}$=$R^{10}$ or H, and X=O, S, and $NR^{11}$.

$R^8$ and $R^9$ are also independently chosen from aryl, aralkyl, heteroaryl of 5- or 6-membered rings containing up to 4 atoms of any of O, S, or N and heteroaralkyl, substituted with from 0 to 3 of halo, alkyl, $CF_3$, $OR^{11}$, $NR_2^{11}$, $CO_2R^{11}$, $CONR_2^{11}$, $COR^{11}$, CN, $OCOR^{11}$, $NR^{11}C(X)R^{11}$, $R^{11}S$, $R^{10}SO$, or $R^{10}SO_2$.

$R^8$ and $R^9$ are also independently chosen from $OR^{11}$, $NR_2^{11}$, $CO_2R^{11}$, $CONR_2^{11}$, $COR^{11}$, CN, $OCOR^{11}$, $NR^{11}C(X)R^{11}$, $R^{11}S$, $R^{10}SO$, or $R^{10}SO_2$.

$R^8$ and $R^9$ may also be joined to form a ring of from 5 to 7 members which contain from 0 to 2 of O, N, S, SO, or $SO_2$, in any combination.

A preferred embodiment of this class comprises compounds wherein $R^8$ and $R^9$ are chosen from H or lower alkyl substituted with 0 or 1 of OH, alkoxy, $NH_2$, mono- or dialkylamino, $NR^{11}C(X)R^{11}$, $N_3$, or $R^{10}SO_2O$. $R^8$ and $R^9$ are also chosen from phenyl, benzyl, pyridyl, pyridylmethyl, thienyl, or thienylmethyl substituted with from 0 to 2 of F, Cl, Br, $CF_3$, $OR^{11}$, $NR_2^{11}$, $OCOR^{11}$, or $NR^{11}C(X)R^{11}$. $R^8$ and $R^9$ may also be joined to form a ring of 5 or 6 members containing 0 or 1 O or N.

The most preferred compounds of this class are listed below.

| $R^8$ | $R^9$ | $R^a$ |
|---|---|---|
| $CH_2CH_2OH$ | H | Bzl, PNB, Na |
| $CH_2CH_2CH_2OH$ | H | Bzl, PNB, Na |
| $CH_2CH_2OSO_2CH_3$ | H | PNB |
| $CH_2CH_2N_3$ | H | PNB |
| OEt | H | PNB, Na |
| H | OEt | PNB, Na |
| $NEt_2$ | $CH_3$ | PNB |

2. Triazolines

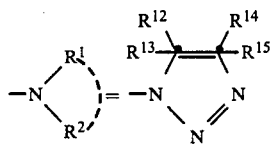

The substituents $R^{12}$, $R^{13}$, $R^{14}$, and $R^{15}$ are independently chosen from 1 to 4 of H, alkyl, alkenyl, and aralkynyl substituted with from 0 to 2 of halo, $OR^{11}$, $NR_2^{11}$, $CO_2R^{11}$, $CONR_2^{11}$, CN, $OCOR^{11}$, $COR^{10}$, $NR^{11}C(X)R^{11}$, $R^{11}S$, $R^{10}SO$, and $R^{10}SO_2$ wherein $R^{10}$, $R^{11}$, and X are as defined in Part 1.

$R^{12}$, $R^{13}$, $R^{14}$, and $R^{15}$ may also be aryl, aralkyl, heteroaryl, or heteroaralkyl of 5- or 6-membered rings containing up to 4 atoms of any of O, N, or S, substituted with from 0 to 3 of halo, alkyl, $CF_3$, $OR^{11}$, $NR_2^{11}$, $CO_2R^{11}$, $CONR_2^{11}$, $COR^{11}$, CN, $OCOR^{11}$, $NR^{11}C(X)R^{11}$, $R^{11}S$, $R^{10}SO$, or $R^{10}SO_2$.

$R^{12}$, $R^{13}$, $R^{14}$, and $R^{15}$, may also be chosen from 0 to 2 of $OR^{10}$, $NR_2^{10}$, $CO_2R^{11}$, CN, $COR^{11}$, $OCOR^{11}$, $NR^{11}C(X)R^{11}$, $R^{11}S$, $R^{10}SO$, and $R^{10}SO_2$.

$R^{12}$ and $R^{14}$ and/or $R^{13}$ and $R^{15}$ may be joined to form one or two rings each containing from 5 to 7 members containing from 0 to 2 of O, N, S, SO, or $SO_2$, provided that the total number of heteroat in both rings is not more than 2.

A preferred embodiment of this class comprises compounds wherein $R^{12}$, $R^{13}$, $R^{14}$, and $R^{14}$ are independently chosen from 1 to 4 of H or alkyl substituted with 0 or 1 of OH, alkoxyl, acyloxy, amino, mono- and dialkylamino, or $NR^{11}C(X)R^{11}$.

$R^{12}$, $R^{13}$, $R^{14}$, and $R^{15}$, are also chosen from phenyl, benzyl, pyridyl, pyridylmethyl, thienyl, or thienylmethyl substituted with from 0 to 2 of halo, $OR^{11}$, $NR_2^{11}$, $OCO^{11}$, or $NR^{11}C(X)R^{11}$.

$R^{12}$ and $R^{14}$ may be joined to form a cis-fused ring of 5 or 6 atoms containing from 0 to 2 of O, N, S, SO, or $SO_2$.

The most preferred compounds of this class are listed below.

| $R^{12}/R^{14}$ | $R^{13}$ | $R^{15}$ | $R^a$ |
|---|---|---|---|
| —CH$_2$CH$_2$O— | H | H | Bzl, PNB |
| —CH$_2$CH$_2$CH$_2$O— (cis-fused) | H | H | Bzl, PNB |

3. Aziridines

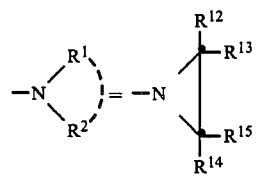

The substituents $R^{12}$, $R^{13}$, $R^{14}$, and $R^{15}$ are independently chosen from 1 to 4 of H, alkyl, alkenyl, or alkynyl substituted with from 0 to 2 of halo, $OR^{11}$, $NR_2^{11}$, $CO_2R^{11}$, $CONHR_2^{11}$, $COR^{11}$, $NR^{11}C(X)R^{11}$, $R^{11}S$, R SO, and R $SO_2$ wherein $R^{10}$, $R^{11}$, and X are as defined in Part 1.

$R^{12}$, $R^{13}$, $R^{14}$, and $R^{15}$ are also chosen from aryl, aralkyl, heteroaryl, and heteroaralkyl of rings of 5 or 6 members containing from 0 to 4 atoms of O, N, or S, substituted with from 0 to 3 of halo, $OR^{11}$, $NR_2^{11}$, $OCOR^{11}$, $NR^{11}C(X)R^{11}$, $COR^{11}$, $CO_2R^{11}$, or $CF_3$.

$R^{12}$, $R^{13}$, $R^{14}$, and $R^{15}$ may also be chosen from 0 to 2 of $OR^{10}$, $OR^{11}$, $NR^{11}C(X)R^{11}$, CN, $COR^{11}$, $CO_2R^{11}$, $CONR_2^{11}$, $SR^{10}$, $R^{10}SO$, $R^{10}SO_2$.

$R^{12}$ and $R^{14}$ and/or $R^{13}$ and $R^{15}$ may be joined together in 1 or 2 rings of 5 to 7 members containing from 0 to 2 of O, N, S, SO, or $SO_2$ provided that the number of heteroatoms in both rings is no more than 4, and that a heterocyclic N atom occurs α to the bridge with the aziridine only in an acylated form, viz as $R^{11}NC(X)R^{11}$ above.

A preferred embodiment of this class comprises compounds wherein $R^{12}$, $R^{13}$, $R^{14}$, and $R^{15}$ are independently chosen from 1 to 4 of H or alkyl substituted with 0 or 1 of OH, alkoxyl, acyloxy, amino, mono- and dialkylamino, or $NR^{11}C(X)R^{11}$.

$R^{12}$, $R^{13}$, $R^{14}$, and $R^{15}$ are also chosen from 1 to 4 of phenyl, benzyl, pyridyl, pyridylmethyl, thienyl, or thienylmethyl substituted with from 0 to 2 of halo, $OR^{11}$, $NR_2^{11}$, $OCOR^{11}$, or $NR^{11}C(X)R^{11}$.

$R^{12}$ and $R^{14}$ may also be joined to form a cis-fused ring of 5 or 6 atoms containing from 0 to 2 of O, N, S, SO, or $SO_2$, provided that a heterocyclic N atom α to the bridge with the aziridine occurs only in an acylated form, viz as $NR^{11}C(X)R^{11}$ above.

The most preferred examples of this class are listed below.

| $R^{12}$ | $R^{13}$ | $R^{14}$ | $R^{15}$ | $R^a$ |
|---|---|---|---|---|
| OAc | H | H | H | Bzl, PNB |
| CO$_2$Et | H | H | H | PNB, Na |
| OAc | CH$_3$ | H | H | PNB, Na |
| *CH$_3$ | H | Cl | H | PNB |
| *CH$_3$ | H | H | Cl | PNB |

*E- and Z-isomers

As noted above, the compounds of the present invention may also generally be represented by the following structural formula:

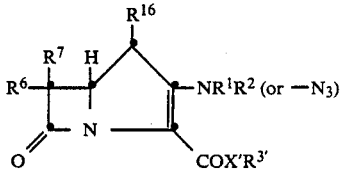

wherein X' is oxygen, sulfur or NR' (R' is hydrogen or loweralkyl having from 1 to 6 carbon atoms); and $R^{3'}$ is hydrogen, or, inter alia, is representatively selected to provide the pharmaceutically acceptable salt, ester, anhydride ($R^{3'}$ is acyl), and amide moieties known in the bicyclic β-lactam antibiotic art; $R^{3'}$ may also be a readily removable blocking group.

Identification of the Radical —COX'R$^{3'}$

In the generic representation of the compounds of the present invention (I, above), the radical represented by —COX'R$^{3'}$ is, inter alia, —COOH (X' is oxygen and $R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and nuclear analogues thereof. By the term "pharmaceutically acceptable ester anhydride and amide derivative thereof" as used herein is meant to include all of the compounds covered by the description of —COX'R³'.

Suitable, but representative, blocking esters R³' (X=O) include those selected from the following list which is representative:

(i) R³'=CR$^a$R$^b$R$^c$ wherein at least one of R$^a$, R$^b$, and R$^c$ is an electrondonor, e.g., p-methoxyphenyl. The remaining R$^a$, R$^b$ and R$^c$ groups may be hydrogen or organic substituting groups. Suitable ester groups of this type include p-methoxybenzyloxycarbonyl.

(ii) R³'=CR$^a$R$^b$R$^c$ wherein at least one of R$^a$, R$^b$ and R$^c$ is an electron-attracting group, e.g., p-nitrophenyl, trichloromethyl, vinyl, acetyl, and o-nitrophenyl. Suitable esters of this type include p-nitrobenzyloxycarbonyl, allyloxycarbonyl, acetonyloxycarbonyl, and 2,2,2-trichloroethoxycarbonyl.

(iii) R³'=CR$^a$R$^b$R$^c$ wherein at least two of R$^a$, R$^b$ and R$^c$ are hydrocarbon such as alkyl, e.g., methyl or ethyl, or aryl, e.g., phenyl and the remaining R$^a$, R$^b$ and R$^c$ group, if there is one, is hydrogen. Suitable esters of this type include t-butyloxycarbonyl, diphenylmethoxycarbonyl and triphenylmethoxycarbonyl.

Silyl esters. This category of blocking groups, may conveniently be prepared from a halosilane of the formula: R³$^4$SiX' wherein X' is a halogen such as chloro or bromo and R$^4$ is alkyl, having 1-6 carbon atoms, phenyl, or phenylalkyl.

Pharmaceutically acceptable carboxyl derivatives of the present invention are those derived by reacting I with alcohols, acylating reagents and the like. For example, esters and amides of interest are the above-listed starting materials and final products having the —COX'R³' group at the 3-position; wherein X' is oxygen, sulfur or NR' (R' is H or R³'), and R³' is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl, diethylaminomethyl, dimethylaminomethyl; alkanoyloxyalkyl wherein the alkanoyloxy portion is straight or branched and has 1-6 carbon atoms and the alkyl portion has 1-6 carbon atoms, such as pivaloyloxymethyl, 1-acetoxyethyl, acetoxymethyl, ethoxycarbonyloxymethyl, 1-(ethoxycarbonyloxy)ethyl, 1-pivaloyloxyethyl; haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, 4-butenyl, and 4-methyl-2-oxo-1,3-dioxalen-5-ylmethyl; aralkyl and lower alkoxyl- and nitro-substituted aralkyl such as benzyl, benzhydryl, o-nitrobenzyl, p-methoxybenzyl, and p-nitrobenzyl; phthalidyl; phthalimidomethyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

group. Representatives of such amides are those wherein R' is selected from the group consisting of hydrogen and alkyl such as methyl and ethyl.

The most preferred —COX'R³' radicals of the present invention are those wherein (relative to Structure I above), X' is oxygen and R³' is hydrogen; loweralkyl having 1-4 carbon atoms; lower alkenyl such as 3-methylbutenyl, 4-butenyl, allyl, and the like; benzyl and substituted benzyl such as p-nitrobenzyl; pivaloyloxymethyl; 3-phthalidyl; 1-(ethoxycarbonyloxy)ethyl; 4-methyl-2-oxo-1,3-dioxalen-5-ylmethyl; and phenacyl.

The novel compounds in the different chemical classes of the present disclosure are believed to be valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella pneumoniae, Bacillus proteus, Salmonella typhosa Psuedomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of prinicipal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semisolid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described herein, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above, schematic reaction diagram for the total synthesis of the defined antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. Temperature is in °C. The compounds of Examples 1–23 were prepared in the racemic form. By starting with the appropriate enantiomer of the starting materials, these compounds can be prepared having the desired 5R configuration. Alternatively, the racemic products can be separated into their enantiomers using standard methods in the art.

EXAMPLE 1

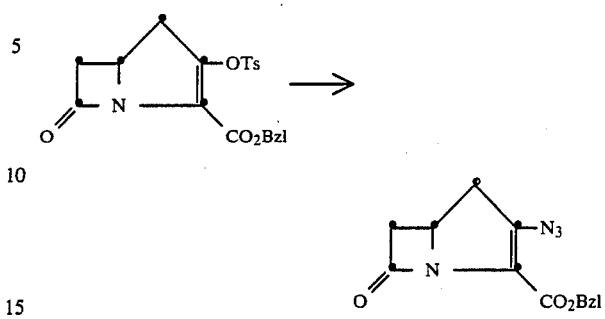

Preparation of Benzyl 2-Azido-carbapen-2-em-3-carboxylate(1)

Method 1.

Potassium azide (11.6 mg, 143. micromol) was added to a stirred ambient temperature solution of benzyl 2-(p-toluenesulfonyloxy)-carbapen-2-em-3-carboxylate (20.0 mg, 48.4 micro mol) prepared according to the analogous procedure described in U.S. Pat. No. 4,424,230, hereby incorporated by reference for this particular purpose, and 1, 4, 7, 10, 13, 16-hexaoxacyclooctadecane (12.8 mg, 48.4 micro mol) in anhydrous acetonitrile (1.0 ml) and dichloromethane (0.2 ml). After 1 hour the mixture was applied to two 20 cm×20 cm 250 micron silica gel preparative thin layer chromatography plates and developed with 3:2 (v/v) toluene-ethyl acetate. The band centered at $R_f$ 0.6 was eluted with ethyl acetate and the elulate was evaporated under vacuum to provide 9.2 mg (67%) benzyl-2-azido-carbapen-2-em-3-carboxylate as a pale yellow glass. The glass was crystallized from 5:1 (v/v) diethyl etherdichloromethane to provide pale yellow rosettes of needles, m.p. 84°–85° C. (dec); I.R. (neat film): 2110, 1785, 1710, 1605, 1285, 1210, 1190 cm$^{-1}$; NMR (CDCl$_3$):$\delta$(del) 2.99 dd (J$_1$=3 Hz, J$_2$=16 Hz, 1H), 3.07 d (J=9 Hz, 2H), 3.52 dd (J$_1$=5 Hz, J$_2$=16 Hz, 1H), 4.25 m (1H), 5.30 d (J=8 Hz, 1H), 5.33 d (J=8 Hz, 1H), 7.37 m (5H); UV (CH$_2$Cl$_2$) $\lambda_{max}$ ($\epsilon$): 310 (10,000) nm; MS (m/e): 256 (M$^+$−N$_2$), 243, 228, 214, 178, 162, 160, 127, 120, 107.

Method 2

Potassium azide (3.2 mg, 39 micromol) was added to a stirred, 0° C. solution of benzyl 2-(p-nitrobenzenesulfonyloxy)-carbapen-2-em-3-carboxylate (5.1 mg, 12 micromol) in anhydrous 5:1 (v/v) acetonitriledichloromethane. After 10 min. the mixture was applied to one 10 cm×20 cm 250 micron silica gel thin layer chromatography plate and developed with diethyl ether. The band centered at R$_f$0.5 was eluted with ethyl acetate and the eluate was evaporated under vacuum to provide 1.2 mg (37%) benzyl 2-azidocarbapen-2-em-3-carboxylate.

EXAMPLE 2

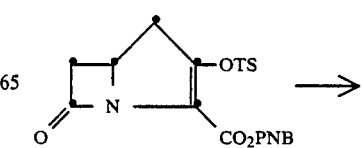

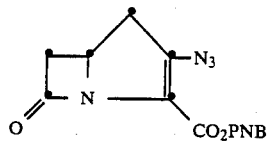

Preparation of p-Nitrobenzyl 2-Azido-carbapen-2-em-3-carboxylate(2)

Method 1

Potassium azide (159 mg, 1.96 mmol) was added to a stirred, 0° C. solution of p-nitrobenzyl 2-(p-toluenesulfonyloxy)-carbapen-2-em-3-carboxylate (300 mg, 0.655 mmol) prepared by the procedure described in U.S. Pat. No. 4,424,230, hereby incorporated by reference for this particular purpose and 1, 4, 7, 10, 13, 16-hexaoxacyclooctadecane (173 mg, 0.655 mmol) in anhydrous acetonitrile (13.5 ml) and dichloromethane (2.7 ml). After 1.5 hours the mixture was filtered through florisil, the florisil was washed with ethyl acetate (150 ml), and the combined filtrate and wash were evaporated to dryness under vacuum to provide 203 mg (94%) solid p-nitrobenzyl 3-azido-carbapen-2-em-3-carboxylate. Recrystallization from ethyl acetate afforded white crystals, m.p. 77° C. (dec); I.R.: 2110, 1785, 1710, 1605, 1520, 1350, 1285, 1210, 1190, 1085 cm$^{-1}$; NMR (CDCl$_3$): δ 3.02 dd ($J_1$=3 Hz, $J_2$=16.5 Hz, 1H), 3.11 d (J=9 Hz, 2H), 3.56 dd ($J_1$=5 Hz, $J_2$=16.5 Hz, 1H), 4.27 tdd ($J_1$=9 Hz, $J_2$=3 Hz, $J_3$=5 Hz, 1H), 5.28 d (J=13.5 Hz, 1H), 5.45 d (J=13.5 Hz, 1H), 7.64 d (J=8 Hz, 2H), 8.24 d (J=8 Hz, 2H); UV (CH$_2$CH$_2$) $\lambda_{max}$: 269, 299 nm; M.S. (m/e): 329 (M+), 315, 301, 287, 255, 136.

Method 2

Diphenyl chlorophosphate (10.9 microliter, 52.6 micromol) was added to a stirred, 0° C. solution of a p-nitrobenzyl 2-oxo-carbapenam-3-carboxylate (15.4 mg, 50.6 micromol), 4-dimethylaminopyridine (1.3 mg, 11 micromol), and diisopropylethylamine (10.4 microliter, 59.7 micromol) in anhydrous acetonitrile (500 microliter). After 5 min., potassium azide (12.6 mg, 155 micromol), and 1, 4, 7, 10, 13, 16-hexaoxacyclooctadecane (13.3 mg, 50.3 micromol) were added. After an additional 5 min. the mixture was washed three times with water, dried over anhydrous magnesium sulfate, filterd, and evaporated under vacuum. The residue was applied to one 20 cm×20 cm 250 micron silica gel preparative thin layer chromatography plate and developed with diethyl ether. Elution with ethyl acetate and evaporation of the eluate under vacuum provided 3.2 mg (19%) p-nitrobenzyl 2-azido-carbapen-2-em-3-carboxylate.

EXAMPLE 3

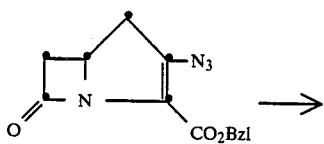

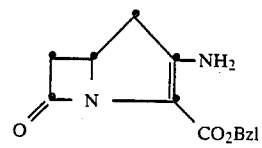

Preparation of Benzyl 2-Amino-carbapen-2-em-3-carboxylate (3)

An ambient temperature mixture of benzyl 2-azido-carbapen-2-em-3-carboxylate (7.7 mg, 27 micromol) and palladium on calcium carbonate poisoned with lead (12.8 mg) in dry dioxane (0.80 ml) containing t-butanol (50 microliter) was stirred while hydrogen was bubbled through for 20 min. The mixture was filtered and the solid washed with diethyl ether (3×0.5 ml). The combined filtrate and washes were concentrated to 0.5 ml under vacuum, and the residue was chromatographed on one 20 cm×20 cm 250 micron silica gel preparative thin layer chromatography plate developed with 1:1 (v/v) toluene-ethyl actetate. The band centered at $R_f$ 0.2 was eluted with ethyl acetate and the eluate was evaporated under vacuum to provide 2.6 mg (37%) benzyl 2-amino-carbapen-2-em-3-carboxylate as a light yellow glass; I.R. (neat film): 3450, 3330, 1780, 1690 cm$^{-1}$; NMR (CDCl$_3$): δ 2.81 dd ($J_1$=4 Hz, $J_2$=16 Hz, 1H), 2.93 m (2H), 3.21 dd ($J_1$=5 Hz, $J_2$=16 Hz, 1H), 5.25 d (J=13 Hz, 1H), 5.32 d (J=13 Hz, 1H), 7.37 m (5H).

EXAMPLE 4

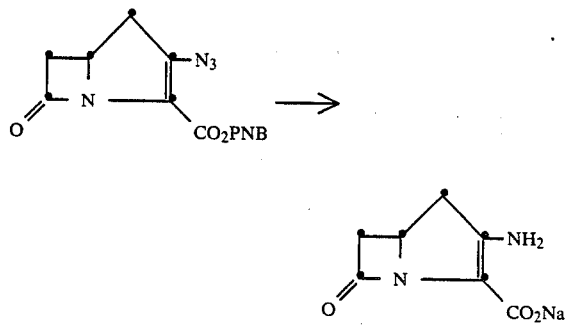

Preparation of Sodium 2-Amino-carbapen-2-em-3-carboxylate (4)

A solution of p-nitrobenzyl 2-azido-carbapen-2-em-3-carboxylate (3.3 mg, 10 micromol) in dioxane (300 microliter), deionized water (180 microliter), absolute ethanol (25 µl), and aqueous sodium bicarbonate solution (20 microliter of 0.5M) was shaken with 10% palladium on charcoal (3.3 mg) under hydrogen (50 psig) at ambient temperature for 40 min. The mixture was centrifuged and the pellet was washed with deionized water (3×0.3 ml). The combined supernates were extracted with ethyl acetate (3×0.4 ml) and lyophilized to provide sodium 2-amino-carbapen-2-em-3-carboxylate.

EXAMPLE 5

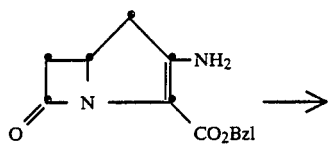

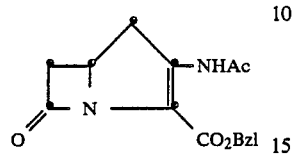

Preparation of Benzyl
2-Acetamido-carbapen-2-em-3-carboxylate (5)

A stirred, 0° C. solution of benzyl 2-aminocarbapen-2-em-3-carboxylate (3.7 mg, 14 micromol) in dry dichloromethane (200 microliter) was treated sequentially with 4-dimethylaminopyridine (5.2 mg, 43 micromol) and acetyl chloride (3.1 microliter, 3.3 mg, 42 micromol). After 3.5 hours the mixture was applied to one 10 cm×20 cm 250 micron silica gel preparative thin layer chromatography plate and developed with 3:1 (v/v) ethyl acetate-ether. The band centered at $R_f$ 0.15 was eluted with ethyl acetate and the eluate was evaporated under vacuum to provide 0.6 mg (14%) benzyl 2-acetamido-carbapen-2-em-carboxylate; IR: 1770, 1725, 1605, 1210 cm$^{-1}$; NMR (CDCl$_3$): δ 2.10 s (CH$_3$CO), 7.37 (Ar); UV (CH$_2$Cl$_2$) $\lambda_{max}$ (ε): 300 (8000) nm.

EXAMPLE 6

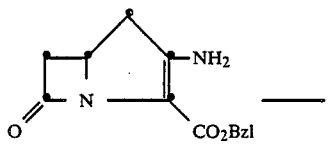

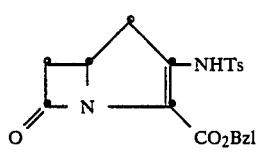

Preparation of Benzyl
2-(p-Toluenesulfonamido)carbapen-2-em-3-carboxylate (6)

p-Toluenesulfonic anhydride (19.2 mg, 58.5 micromol) was added to a stirred, 0° C. solution of benzyl 2-amino-carbapen-2-em-3-carboxylate (3.4 mg, 13 micromol) and diisopropylethylamine (37 microliter, 25 mg, 19.5 micromol) in dry dichloromethane (0.4 ml). After 2 hours the mixture was applied to one 20 cm×20 cm 250 micron silica gel preparative thin layer chromatography plate and developed with 2:1 (v/v) diethyl ether-ethyl acetate. The ninhydrin negative product band was collected and eluted with ethyl acetate. Evaporation of the eluate under vacuum provided 0.3 mg (6%) benzyl 2-(p-toluenesulfonamido)carbapen-2-em-3-carboxylate; IR (neat film); 3585, 3350, 1780, 1745, 1625, 1360, 1190 cm$^{-1}$.

EXAMPLE 7

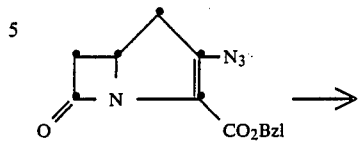

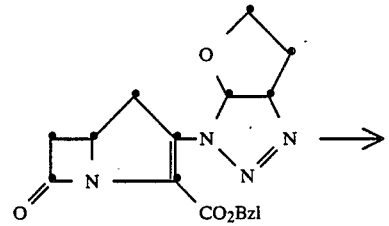

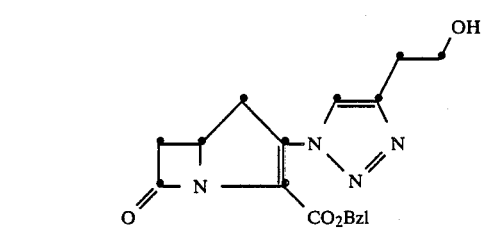

Preparation of Benzyl
2-(2,3,4-triaza-8-oxabicyclo[3.2.0]oct-3-en-2-yl)-carbapen-2-em-3-carboxylate (7) and Benzyl
2-(4-[2-Hydroxyethyl]-1,2,3-triazol-1-yl)-carbapen-2-em-3-carboxylate (8)

A mixture of benzyl 2-azido-carbapen-2-em-3-carboxylate (14.3 mg, 50.3 micromol) and 2,3-dihydrofuran (100 microliter) in anhydrous dichloromethne (0.75 ml) containing excess sodium bicarbonate was kept 18 hours at −4° C. One third of the reaction mixture was filtered through florisil and the florisil was washed with ethyl acetate (25 ml). The combined filtrate and wash were evaporated under vacuum to provide 5.5 mg (96%) of a mixture of isomers of benzyl 2-(2,3,4-triaza-8-oxabicyclo[3.2.0]oct-3-en-2-yl)-carbapen-2-em-3-carboxylate; $R_f$ (SiO$_2$, Et$_2$O): 0.60; IR (CH$_2$Cl$_2$): 1780, 1710, 1590, 1510, 1275, 1210, 1070 cm$^{-1}$; NMR (CDCl$_3$): δ 2.32 m and 2.50 m (2H), 2.94 dd (J$_1$=3 Hz, J$_2$=17 Hz) (1H), 3.14 m (1H), 3.24 m (1H), 3.48 m (2H), 3.60 m (1H), 3.84 m (1H), 4.10 m (1H), 5.30 m (2H), 6.72 d (J=6 Hz) and 6.81 d (J=6 Hz)(1H), 7.37 m (5H). The remainder of the reaction mixture was kept 2 weeks at −4° C. to provide a solution of benzyl 2-(4-[2-hydroxyethyl]-1,2,3-triazol-1-yl)-carbapen-2-em-3-carboxylate, $R_f$ (SiO$_2$, Et$_2$O): 0.10.

EXAMPLE 8

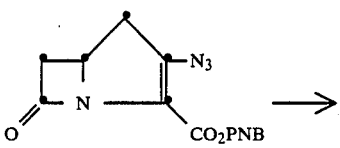
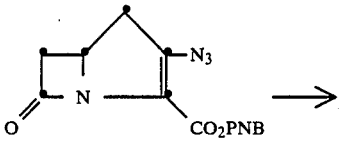

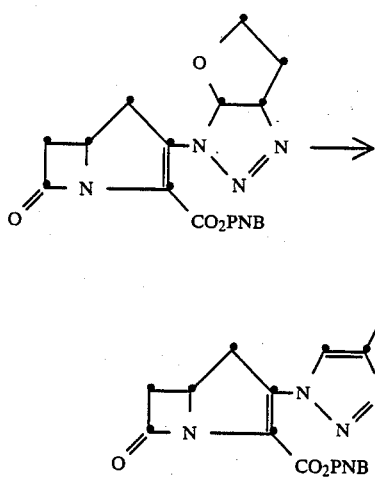

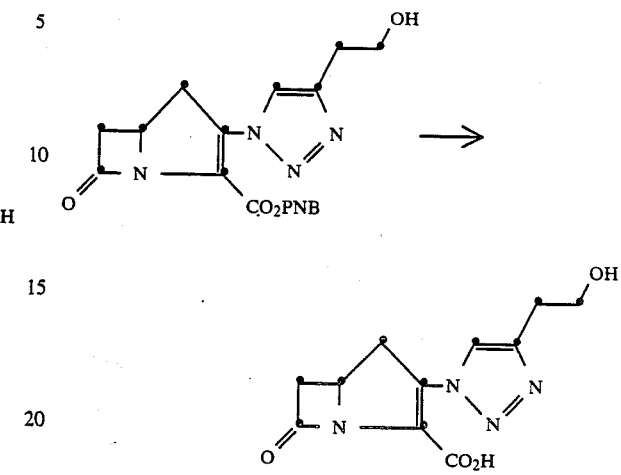

EXAMPLE 9

Preparation of p-Nitrobenzyl 2-(2,3,4-Triaza-8-oxabicyclo[3.2.0]oct-3-en-2-yl)-carbapen-2-em-3-carboxylate (9) and p-Nitrobenzyl 2-(4-[2-Hydroxyethyl]-1,2,3-triazol-1-yl)-carbapen-2-em-3-carboxylate (10)

A mixture of p-nitrobenzyl 2-azido-carbapen-2-em-3-carboxylate (26.4 mg, 80.2 micromol) and 2,3-dihydrofuran (0.1 ml) in dry dichloromethane (2.0 ml) containing excess sodium bicarbonate was kept 2.5 days at 4° C. Approximately one-fourth of the reaction mixture was filtered through florisil and the florisil was washed with ethyl acetate (25 ml). The combined filtrate and wash was evaporated under vacuum to provide 8.5 mg of a mixture of isomers of p-nitrobenzyl 2-(2,3,4-triaza-8-oxabicyclo[3.2.0]oct-3-en-2-yl)-carbapen-2-em-3-carboxylate, $R_f$ (SiO$_2$, Et$_2$O): 0.43; IR (CH$_2$Cl$_2$): 1780, 1715, 1605, 1520, 1350, 1280, 1075 cm$^{-1}$; NMR (CDCl$_3$): δ 2.36 m and 2.54 m (2H), 2.97 dd ($J_1=3$ Hz, $J_2=16$ Hz) and 3.00 dd ($J_1=3$ Hz, $J_2=16$ Hz) (1H), 3.15 m (1H), 3.26 m (1H), 3.53 m (2H), 3.64 m (1H), 3.90 m (1H), 4.14 m (1H), 5.26 d (J=14 Hz) and 5.52 d (J=14 Hz) and 5.32 d (J=15 Hz) and 5.46 d (J=15 Hz) (2H), 5.70 d (J=6 Hz) and 5.80 d (J=6 Hz) (1H), 7.67 bd (J=9 Hz, 2H), 8.14 d (J=9 Hz, 2H). The remainder of the reaction mixture was kept 1 week at 4° C., applied to one 20 cm×20 cm 250 micron silica gel thin layer preparative chromatography plate, and developed with 17:3 (v/v) diethyl ether-ethyl acetate. Product was eluted with ethyl acetate and the eluate was evaporated under vacuum to provide 6.4 mg p-nitrobenzyl 2-(4-[2-hydroxyethyl]-1,2,3-triazol-1-yl)-carbapen-2-em-3-carboxylate; $R_f$ (SiO$_2$, Et$_2$O): 0.08; IR (neat): 3600–3200, 1775, 1710, 1670, 1615, 1520, 1350, 1295, 1215 cm$^{-1}$; NMR (CDCl$_3$): δ 2.52 t (J=6.5 Hz, 2H), 2.96 dd ($J_1=3$ Hz, $J_2=16.5$ Hz, 1H), 3.35 dd ($J_1=8$ Hz, $J_2=20$ Hz, 1H), 3.54 dd ($J_1=5.5$ Hz, $J_2=16.5$ Hz, 1H), 3.71 t (J=6.5 Hz, 2H), 3.82 dd ($J_1=10$ Hz, $J_2=20$ Hz, 1H), 4.20 m (1H), 5.28 d (J=14 Hz, 1H), 5.49 d (J=14 Hz, 1H), 7.66 d (J=9 Hz, 2H), 8.26 d (J=9 Hz, 2H), 9.84 s (1H).

Preparation of 2-(4-[2-Hydroxyethyl]-1,2,3-triazol-1-yl)-carbapen-2-em-3-carboxylic acid (11)

A solution of p-nitrobenzyl 2-(4-[2-hydroxyethyl]-1,2,3-triazol-1-yl)-carbapen-2-em-3-carboxylate (3.5 mg, 8.8 micromol) in dioxane (300 microliter), deionized water (180 microliter), absolute ethanol (24 microliter), and pH 7.0 4-morpholinepropanesulfonic acid buffer (60 microliter of 0.5M) was shaken with 10% (w/w) palladium on charcoal (7.0 mg) under hydrogen (50 psig) at ambient temperature. After 40 min. the mixture was centrifuged and the pellet washed with deionized water (3×0.5 ml). The combined supernate and washes were extracted with ethyl acetate (3×0.5 ml) and concentrated under vacuum to provide 0.5 ml of a solution of 2-(4-[2-hydroxyethyl]-1,2,3-triazol-1-yl)-carbapen-2-em-3-carboxylic acid, UV $\lambda_{max}$ 299 nm which quenched upon addition of hydroxylamine hydrochloride and dipotassium hydrogen phosphate.

EXAMPLE 10

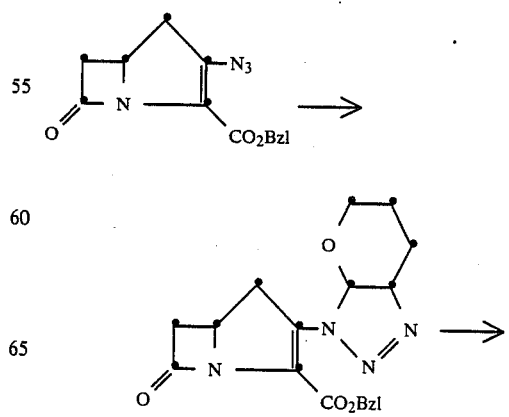

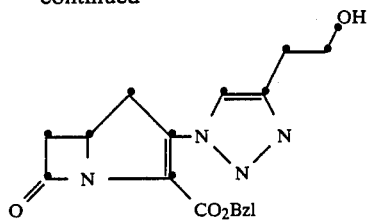

Preparation of Benzyl 2-(7,8,9-Triaza-2-oxabicyclo[4.3.0]non-7-en-9-yl)-carbapen-2-em-3-carboxylate (12) and Benzyl 2-(4-[3-Hydroxypropyl]-1,2,3-triazol-1-yl)-carbapen-2-em-3-carboxylate (13)

A solution of benzyl 2-azido-carbapen-2-em-3-carboxylate (23.9 mg, 84.1 micromol) and dihydropyran (100 microliter) in dry dichloromethane (1.0 ml) containing excess sodium bicarbonate was kept 6 days at 4° C. A t.l.c. (SiO$_2$, Et$_2$O) indicated the presence of a mixture of benzyl 2-(7,8,9-triaza-2-oxabicyclo[4.3.0]non-7-en-9-yl)-carbapen-2-em-3carboxylate (R$_f$ 0.67) and benzyl 2-(4-[3-hydroxypropyl]-1,2,3-triazol-1-yl)-carbapen-2-em-3-carboxylate (R$_f$ 0.16). The latter was isolated by filtering the reaction mixture through florisil, washing the florisil with ethyl acetate (25 ml), evaporating the combined filtrate and wash to dryness under vacuum, and chromatographing the residue on one 20 cm×20 cm 250 micron silica gel preparative thin layer chromatography plate developed with 9:1 (v/v) diethyl ether-ethyl acetate to provide 1.9 mg (6%), IR (CH$_2$Cl$_2$): 3600–3200, 1780, 1725 cm$^{-1}$.

EXAMPLE 11

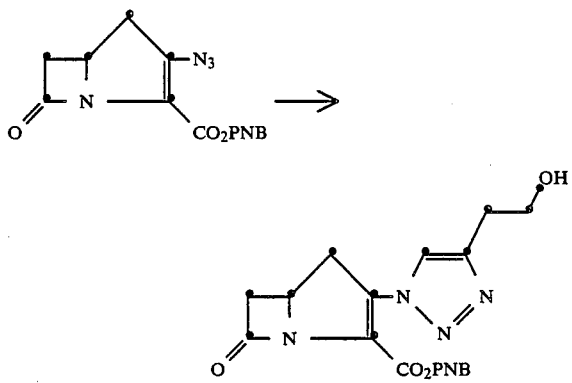

Preparation of p-Nitrobenzyl 2-(4-[3-Hydroxypropyl]-1,2,3-triazol-1-yl)-carbapen-2-em-3-carboxylate (14)

A solution of p-nitrobenzyl 2-azido-carbapen-2-em-carboxylate (27.6 mg, 83.8 micromol) in dihydropyran (1.0 ml) was kept 46 hours at 4° C. and 51 hours at ambient temperature. The reaction mixture was chromatographed on two 20 cm×20 cm 250 micron silica gel preparative thin layer chromatography plates developed with 3:1 (v/v) diethyl ether-ethyl acetate. The band centered at R$_f$0.10 was eluted with ethyl acetate, and the eluate was evaporated under vacuum to provide 8.0 mg (23%) p-nitrobenzyl 2-(4-[3-hydroxypropyl]-1,2,3-triazol-1-yl)-carbapen-2-em-3-carboxylate; IR (CDCl$_3$): 3600–3100, 1775, 1710, 1610, 1520, 1345, 1290, 1215 cm$^{-1}$; NMR (CDCl$_3$): δ 1.78 m (2H), 2.44 t (J=7.5 Hz, 2H), 2.99 dd (J$_1$=3 Hz, J$_2$=17 Hz, 1H), 3.37 dd (J$_1$=8 Hz, J$_2$=20 Hz, 1H), 3.57 dd (J$_1$=5 Hz, J$_2$=17 Hz, 1H), 3.70 bt (J=6 Hz,2H), 3.85 dd (J$_1$=10 Hz, J$_2$=20 Hz, 1H), 4.14 m (1H), 5.31 d (J=14 Hz, 1H), 5.52 d (J=14 Hz, 1H), 7.70 d (J=9 Hz, 2H), 8.31 d (J=9 Hz, 2H), 9.84 s (1H); UV (CH$_2$Cl$_2$) λ$_{max}$ (ε): 272 (6000), 317 (8300) nm.

EXAMPLE 12

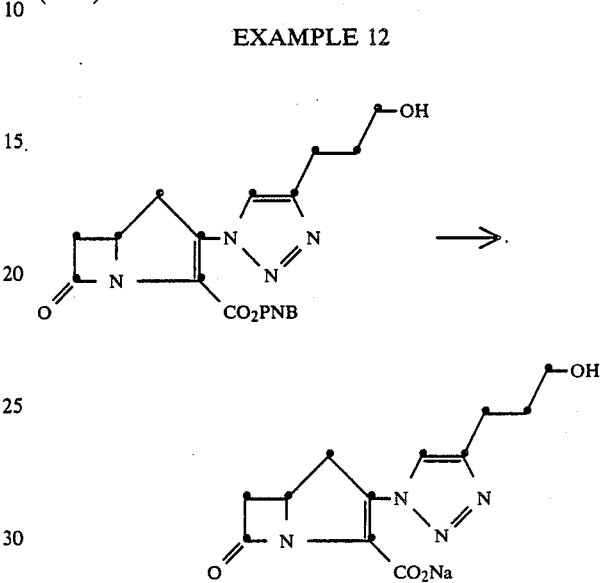

Preparation of Sodium 2-(4-[3-Hydroxypropyl]-1,2,3-triazol-1-yl)-carbapen-2-em-3-carboxylate (15)

A solution of p-nitrobenzyl 3-(4-[3-hydroxypropyl]-1,2,3-triazol-1-yl)-carbapen-2-em-3-carboxylate (6.5 mg, 16 micromol) in dioxane (600 microliter), deionized water (350 microliter), absolute ethanol (50 microliter), and 0.5N aqueous sodium bicarbonate (31 microliter) was shaken with 10% (w/w) palladium on charcoal (6.0 mg) under hydrogen (50 psig) at ambient temperature. After 45 min. the mixture was centrifuged and the pellet washed with deionized water (4×2 ml). The combined supernate and washes were extracted with ethyl acetate (3×4 ml) and concentrated under vacuum to provide 2.0 ml of a solution of sodium 2-(4-[3-hydroxypropyl]-1,2,3-triazol-1-yl)-carbapen-2-em-3-carboxylate; UV λ$_{max}$ 291 nm, which quenched upon addition of hydroxylamine hydrochloride and dipotassium hydrogen phosphate.

EXAMPLE 13

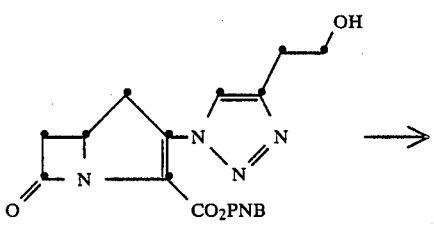

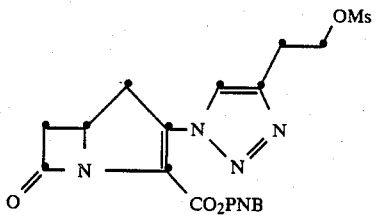

Preparation of p-Nitrobenzyl 2-(4-[2-Methanesulfonyloxyethyl]-1,2,3-triazol-1-yl)-carbapen-2-em-3-carboxylate (16)

A stirred, 0° C. solution of p-nitrobenzyl 2-(4-[2-hydroxyethyl]-1,2,3-triazol-1-yl)-carbapen-2-em-3-carboxylate (49.3 mg, 123 micromol) in dry dichloromethane (8.4 ml) was treated sequentially with diisopropylethylamine (131 microliter, 97.3 mg, 753 micromol) and methanesulfonyl chloride (57.3 microliter, 84.8 mg, 740 micromol). After 15 min. 5% (w/v) aqueous sodium bicarbonate (3 ml) was added, the layers were separated, and the organic phase was washed with water (3.0 ml) and brine (3.0 ml), dried with anhydrous magnesium sulfate, and evaporated under vacuum to provide 60.0 mg p-nitrobenzyl 2-(4-[2-methanesulfonyloxy]-1,2,3-triazol-1-yl)-carbapen-2-em-3-carboxylate; NMR (CDCl$_3$): δ 2.54 t (J=6.5 Hz, 2H), 3.00 dd (J$_1$=3 Hz, J$_2$=17 Hz, 1H), 3.04 s (3H), 3.35 dd (J$_1$=9 Hz, J$_2$=20 Hz, 1H), 3.55 dd (J$_1$=5 Hz, J$_2$=17 Hz, 1H), 3.81 dd (J$_1$=10 Hz, J$_2$=20 Hz, 1H), 4.21 m (1H), 4.30 t (J=6.5 Hz, 2H), 5.30 d (J=14 Hz, 1H), 5.50 d (J=14 Hz, 1H), 7.66 d (J=8 Hz, 2H), 8.26 d (J=8 Hz, 2H), 9.80 s (1H).

EXAMPLE 14

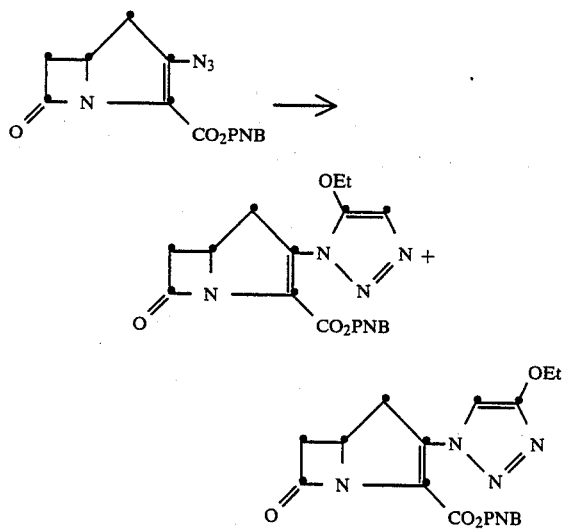

Preparation of p-Nitrobenzyl 2-(5-Ethoxy-1,2,3-triazol-1-yl)-carbapen-2-em-3-carboxylate (17) and p-Nitrobenzyl 2-(4-Ethoxy-1,2,3-triazol-1-yl)-carbapen-2-em-3-carboxylate (18)

A solution of p-nitrobenzyl 3-azido-carbapen-2-em-3-carboxylate (40 mg, 0.12 mmol) in ethoxyacetylene (1 ml) was stirred overnight at ambient temperature. The mixture was applied to two 20 cm×20 cm 250 micron silica gel preparative thin layer chromatography plates and developed with 5:1 (v/v) diethyl ether-ethyl acetate. The band centered at R$_f$0.33 was eluted with ethyl acetate and the eluate was evaporated under vacuum to provide 4.9 mg (10%) of a 9:1 mixture of p-nitrobenzyl 2-(5-ethoxy-1,2,3-triazol-1-yl)-carbapen-2-em-3-carboxylate and p-nitrobenzyl 2-(4-ethoxy-1,2,3-triazol-1-yl)-carbapen-2-em-3-carboxylate; IR (CH$_2$Cl$_2$): 1785, 1735 cm$^{-1}$; MS (m/e): 371, 329, 235, 207, 136; NMR (CDCl$_3$): δ 1.32 t (J=7 Hz, 3H), 3.23 dd (J$_1$=3 Hz, 17 Hz, 1H), 3.44 d (J=9 Hz, 2H), 3.67 dd (J$_1$=6 Hz, J$_2$=17 Hz, 1H), 4.13 q (J=7 Hz, 2H), 4.46 m (1H), 5.28 d (J=13 Hz, 1H), 5.40 d (J=13 Hz, 1H), 7.54 d (J=9 Hz, 2H), 8.26 d (J=9 Hz, 2H), 8.26 s (1H).

EXAMPLE 15

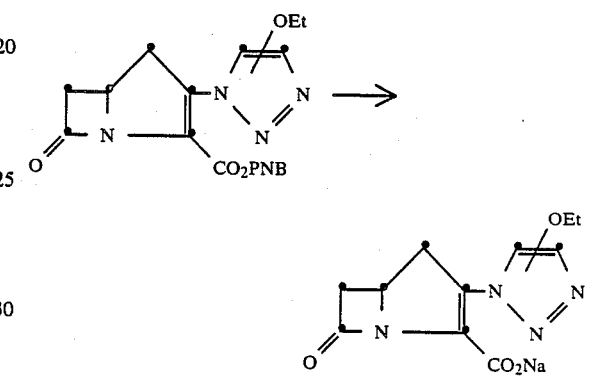

Preparation of Sodium 2-(4- and 5-Ethoxy-1,2,3-triazol-1-yl)-carbapen-2-em-3-carboxylate (19)

A solution of a 9:1 mixture of p-nitrobenzyl 2-(5-ethoxy-1,2,3-triazol-1-yl)-carbapen-2-em-3-carboxylate and p-nitrobenzyl 2-(4-ethoxy-1,2,3 -triazol-1-yl)-carbapen-2-em-3-carboxylate (4.6 mg, 12 micromol) in dioxane (420 microliter), deionized water (250 microliter), absolute ethanol (35 microliter), and 0.5M aqueous sodium bicarbonate (22 microliter), was shaken with 10% (w/w) palladium on charcoal (4.6 mg) under hydrogen (50 psig) at ambient temperature to provide a solution of sodium 2-(4- and 5-ethoxy-1,2,3-triazol-1-yl)-carbapen-2-em-3-carboxylate; UV λ$_{max}$ 316 nm, quenched upon addition of hydroxylamine hydrochloride and dipotassium hydrogen phosphate.

EXAMPLE 16

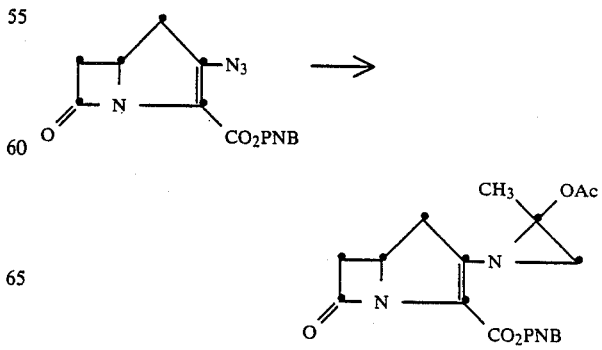

Preparation of p-Nitrobenzyl 2-(2-Acetoxy-2-methylaziridin-1-yl)-carbapen-2-em-3-carboxylate (20)

Two solutions of p-nitrobenzyl 2-azidocarbapen-2-em-3-carboxylate (52 mg and 24 mg, 231 micromol) and 2-acetoxy-1-propene (0.25 ml each) in dichloromethane were kept 2.5 days at ambient temperature. The mixtures were combined, filtered through florisil, and evaporated under vacuum. The residue was chromatographed on four 20 cm×20 cm 250 micron silica gel preparative thin layer chromatography plates developed with 5:1 (v/v) diethyl ether-ethyl acetate. The band centered at $R_f$ 0.25 was eluted with ethyl acetate and the eluate evaporated under vacuum to provide 15.9 mg (17%) p-nitrobenzyl 2-(2-acetoxy-2-methylaziridin-1-yl)-carbapen-2-em-3-carboxylate; IR ($CH_2Cl_2$): 1770, 1735 cm$^{-1}$, NMR ($CDCl_3$): 1.69 s (3H), 2.11 s (3H), 2.16 d (J=7 Hz, 1H), 2.22 d (J=7 Hz, 1H), 2.74 dd (J=8 Hz, $J_2$=17 Hz, 1H), 2.79 dd($J_1$=3 Hz, $J_2$=16 Hz, 1H), 2.84 dd ($J_1$=5 Hz, $J_2$=17 Hz, 1H), 3.21 dd ($J_1$=6 Hz, $J_2$=16 Hz, 1H), 4.30 m (1H), 5.29 d (J=12 Hz, 1H), 5.35 d (J=12 Hz, 1H), 7.57 d (J=9 Hz, 2H), 8.29 d (J=9 Hz, 2H); MS (m/e): 402 (M+), 359, 342, 316, 300, 274, 2H); MS (m/e): 402 (M ) 258, 222.

EXAMPLE 17

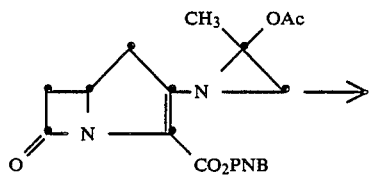

Preparation of Sodium 2-(2-Acetoxy-2-methylaziridine-1-yl)-carbapen-2-em-3-carboxylate (21)

A solution of p-nitrobenzyl 2-(2-acetoxy-2-methylaziridin-1-yl)-carbapen-2-em-3-carboxylate (0.9 mg, 2.3 micromol) in dioxane (100 microliter), deionized water (60 microliter), absolute ethanol (8 microliter), and 0.5M aqueous sodium bicarbonate (5 microliter) was shaken with 10% (w/w) palladium on charcoal (1.1 mg) under hydrogen (50 psig) for 30 min. The mixture was centrifuged and the pellet washed with deionized water (3×100 microliter). The combined supernate and washes were extracted with ethyl acetate (3×0.5 ml) and concentrated under vacuum to provide 420 microliter of a solution of sodium 2-(2-acetoxy-2-methylaziridin-1-yl)-carbapen-2-em-3-carboxylate.

EXAMPLE 18

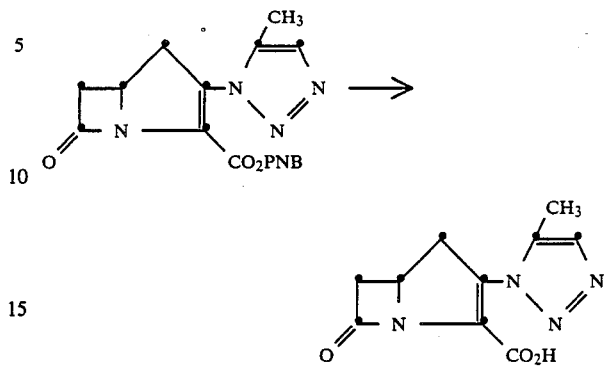

Preparation of 2-(4- and 5-Methyl-1,2,3-triazol-1-yl)-carbapen-2-em-3-carboxylic acid (22)

A solution of a mixture of p-nitrobenzyl 2-(4-methyl-1,2,3-triazol-1-yl)-carbapen-2-em-3-carboxylate and p-nitrobenzyl 2-(5-methyl-1,2,3-triazol-1-yl)-carbapen-2-em-3-carboxylate (0.7 mg) in dioxane (100 microliter), deionized water (60 microliter), absolute ethanol (8.3 microliter), and pH 7.0 0.5M aqueous 4-morpholinepropanesulfonic acid (10.2 microliter) was shaken with 10% (w/w) palladium on charcoal (1.0 mg) under hydrogen (50 psig) at ambient temperature. After 30 min. the mixture was centrifuged and the pellet was washed with deionized water (5×0.5 ml). The combined supernate and washes were extracted with ethyl acetate (3×0.5 ml) and concentrated under vacuum at 0° C. to provide 2.0 ml of a solution of 2-(4-methyl-1,2,3-triazol-1-yl)-carbapen-2-em-3-carboxylic acid and 2-(5-methyl-1,2,3-triazol-1-yl)-carbapen-2-em-3-carboxylic acid, UV $\lambda_{max}$ 295 nm quenched by addition of hydroxylamine hydrochloride and dipotassium hydrogen phosphate.

EXAMPLE 19

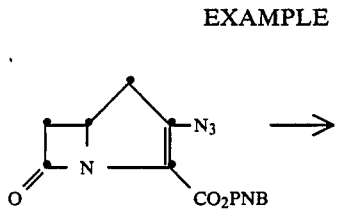

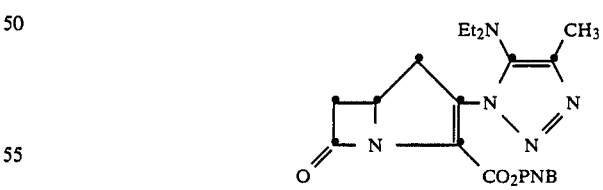

Preparation of p-Nitrobenzyl 2-(5-Diethylamino-4-methyl-1,2,3-triazol-1-yl)-carbapen-2-em-3-carboxylate (23)

A stirred, 0° C. solution of p-nitrobenzyl 2-azido-carbapen-2-em-3-carboxylate (5.9 mg, 18 micromol) in dry dichloromethane (0.30 ml) was treated with 1-diethylaminopropyne (2.5 microliter, 2.0 mg, 18 micromol). After 1.25 hours the mixture was filtered through a 6 cm×4 mm column of florisil and the eluate was evaporated under vacuum. The residue was chromatographed on one 5 cm×20 cm 250 micron silica gel thin layer chromatography plate developed with 5:1 (v/v) dichloromethane-ethyl acetate, and the band centered at $R_f$ 0.30 was eluted with ethyl acetate. The eluate was evaporated under vacuum to provide 1.2 mg (15%) p-nitrobenzyl 2-(5-diethylamino-4-methyl-1,2,3-triazol-1-yl)-carbapen-2-em-3-carboxylate; IR ($CH_2Cl_2$): 1785, 1730 cm$^{-1}$; NMR (CDCl$_3$): δ 0.92 t (J=7 Hz, 6H), 2.30 s (3H), 2.97 q (J=7 Hz, 4H), 3.18 dd ($J_1$=4 Hz, $J_2$=17 Hz, 1H), 3.24 dd ($J_1$=10 Hz, $J_2$=18 Hz, 1H), 3.40 dd ($J_1$=8 Hz, $J_2$=18 Hz, 1H), 3.65 dd ($J_1$=6 Hz, $J_2$=17 Hz, 1H), 4.25 m (1H), 5.22 d (J=14 Hz, 1H), 5.32 d (J=14 Hz, 1H), 7.45 d (J=9 Hz, 2H), 8.22 d (J=9 Hz); MS (m/e): 440, 414, 412, 398, 384, 369, 357, 355, 341, 333.

EXAMPLE 20

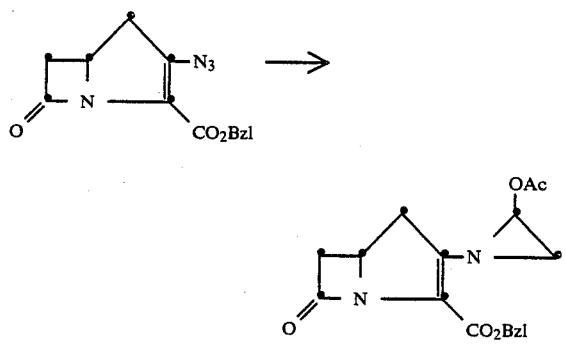

Preparation of Benzyl 2-(2-Acetoxyaziridin-1-yl)-carbapen-2-em-3-carboxylate (24)

A solution of benzyl 2-azido-carbapen-2-em-3-carboxylate (5.3 mg, 19 micromol) and vinyl acetate (100 microliter) in dry dichloromethane (200 microliter) was treated with excess sodium bicarbonate and kept 3 days at ambient temperature. The mixture was filtered through florisil, the florisil was washed with ethyl acetate (25 ml), and the combined filtrate and wash was evaporated under vacuum. The residue was chromatographed on one 20 cm×20 cm 250 micron silica gel preparative thin layer chromatography plate developed with 9:1 (v/v) diethyl ether-ethyl acetate. Product was eluted with ethyl acetate and the eluate evaporated under vacuum to provide 1.2 mg (19%) benzyl 2-(2-acetoxyaziridin-1-yl)-carbapen-2-em-3-carboxylate; IR ($CH_2Cl_2$): 1770, 1735 cm$^{-1}$; NMR (CDCl$_3$): δ 1.92 bt (J=6.5 Hz, 1H), 2.08 t (J=7 Hz, 1H), 2.13 s (3H), 2.70 dd (J, 6 Hz, $J_2$=17 Hz, 1H), 2.76 dd ($J_1$=6 Hz, $J_2$=17 Hz, 1H), 2.86 dd ($J_1$=2 Hz, $J_2$=15 Hz, 1H), 3.24 dd ($J_1$=5 Hz, $J_2$=15 Hz, 1H), 4.16 m (1H), 4.79 bt (J=7 Hz, 1H), 5.17 s (2H), 7.37 m (5H).

EXAMPLE 21

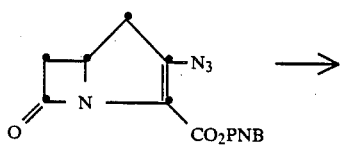

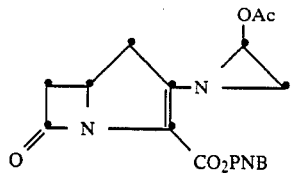

Preparation of p-Nitrobenzyl 2-(2-Acetoxyaziridin-1-yl)-carbapen-2-em-3-carboxylate (25)

A mixture of p-nitrobenzyl 2-azido-carbapen-2-em-3-carboxylate (11.3 mg, 34 micromol), vinyl acetate (0.1 ml), and solid sodium bicarbonate in dry dichloromethane was kept 2 days at ambient temperature, filtered through florisil, and evaporated under vacuum. The residue was chromatographed on one 15 cm×20 cm 250 micron silica gel preparative thin layer chromatography plate developed with 5:1 (v/v) diethyl ether-ethyl acetate. The band centered at $R_f$ 0.20 was eluted with ethyl acetate and the eluate was evaporated under vacuum to provide 5.5 mg (41%) p-nitrobenzyl 2-(2-acetoxyaziridin-1-yl)-carbapen-2-em-3-carboxylate; IR ($CH_2Cl_2$): 1770, 1735 cm$^{-1}$; NMR (CDCl$_3$): δ 1.90 dd ($J_1$=6 Hz, $J_2$=7 Hz, 1H), 2.10 t (J=7 Hz, 1H), 2.13 s (3H), 2.76 bd (J=5 Hz, 2H), 2.85 dd ($J_1$=2.5 Hz, $J_2$=15 Hz, 1H), 3.25 dd ($J_1$=5 Hz, $J_2$=15 Hz, 1H), 4.12 m (1H), 4.87 dd ($J_1$=6 Hz, $J_2$=7 Hz, 1H), 5.27 s (2H), 7.49 d (J=9 Hz, 2H), 8.25 d (J=9 Hz, 2H).

EXAMPLE 22

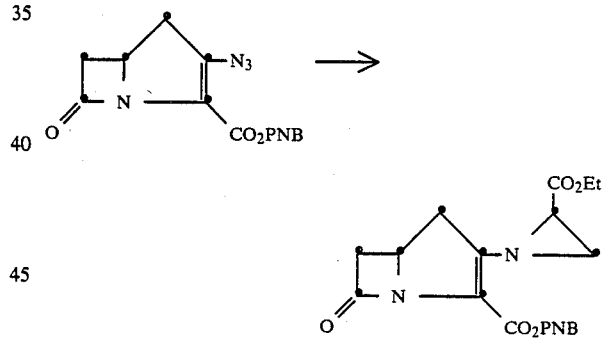

Preparation of p-Nitrobenzyl 2-(2-Carbethoxyaziridin-1-yl)-carbapen-2-em-3-carboxylate (26)

Freshly distilled ethyl acrylate (0.25 ml) was added to a mixture of p-nitrobenzyl 2-azidocarbapen-2-em-3-carboxylate (12.2 mg, 37.1 micromol) and solid sodium bicarbonate in dry dichloromethane (0.25 ml). After 2 days at ambient temperature the mixture was filtered through florisil, the florisil was washed with ethyl acetate (25 ml), and the combined filtrate and wash were evaporated under vacuum. The residue was chromatographed on one 20 cm×20 cm 250 micron silica gel preparative thin layer chromatography plate developed with 4:1 (v/v) diethyl ether-ethyl acetate to provide 5.6 mg (34%) p-nitrobenzyl-2-(2-carbethoxyaziridin-1-yl)-carbapen-2-em-3-carboxylate; $R_f$(SiO$_2$, 4:1 [v/v] Et$_2$O-EtOAc): 0.30; IR ($CH_2Cl_2$): 1780, 1735, 1710, 1605, 1520, 1345, 1180 cm$^{-1}$; NMR (CDCl$_3$): δ 1.30 t (J=7 Hz, 3H), 1.65 bt (J=5 Hz, 1H), 1.93 m (1H), 2.6–2.8 m (4H), 2.95 dd (J₁=5 Hz, J₂=15 Hz, 1H), 4.05 m (1H), 4.21 q (J=7 Hz, 2H), 5.32 s (2H), 7.25 d (J= 9 Hz, 2H), 8.30 d (J=9 Hz, 2H); MS (m/e): 401 (M+), 355, 282, 265, 237, 223.

EXAMPLE 23

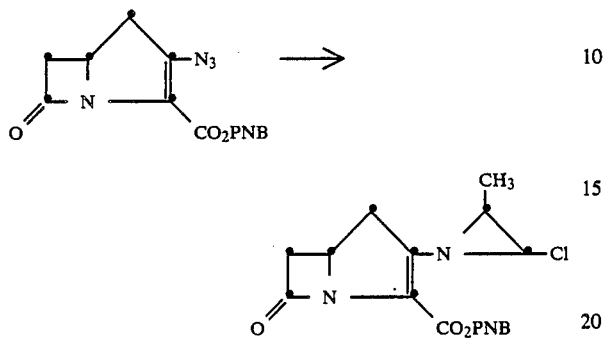

Preparation of p-Nitrobenzyl E- and Z-2-(2-Chloro-3-methylaziridin-1-yl)-carbapen-2-em-3-carboxylate (27)

A freshly distilled 1:1 mixture of E- and Z-1-chloro-1-butene (300 microliter) was added to a mixture of p-nitrobenzyl 2-azido-carbapen-2-em-3-carboxylate (8.1 mg, 25 micromol) and excess solid sodium bicarbonate in dry dichloromethane. After 30 hours at ambient temperature and 2.5 days at 4° C. the mixture was filtered through florisil, the florisil was washed with ethyl acetate, and the combined filtrate and wash were evaporated under vacuum. The residue was chromatographed on one 15 cm×20 cm 250 micron silica gel preparative thin layer chromatography plate developed with 4:1 (v/v) diethyl ether-ethyl acetate to provide 2.0 mg (22%) of a mixture of p-nitrobenzyl E- and Z-2-(2-chloro-3-methylaziridin-1-yl)-carbapen-2-em-3-carboxylate; R$_f$ (SiO₂, 4:1 [v/v] Et₂O-EtOAc): 0.59; IR (CH₂Cl₂): 1770, 1730 cm⁻¹; NMR (CDCl₃): δ 1.34 d (J=7 Hz) and 1.44 d (J=6 Hz, 2H), 2.30 m (1H), 2.78 dd (J₁=3 Hz, J₂=15 Hz, 1H), 2.81 d (J=6 Hz, 2H), 3.28 dd (J₁=6 Hz, J₂=15 Hz, 1H), 3.80 d (J=6 Hz) and 4.14 d (J=6 Hz) (1H), 4.04 m (1H), 5.31 m (2H), 7.56 d (J=9 Hz, 2H), 8.28 d (J=9 Hz, 2H).

EXAMPLE 24A

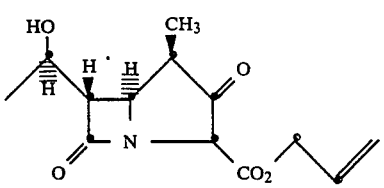

III

Preparation of Allyl (1R,3R,5R,6S)-6-[(R)-1-hydroxyethyl]-1-methyl-2-oxocarbapenam-3-carboxylate The title compound was prepared as detailed below using procedures analogous to those described for the corresponding p-nitrobenzyl ester (see D. H. Shih et al., *Heterocycles*, 21(1), 29–40 (1984)), hereby incorporated by reference for this particular purpose.

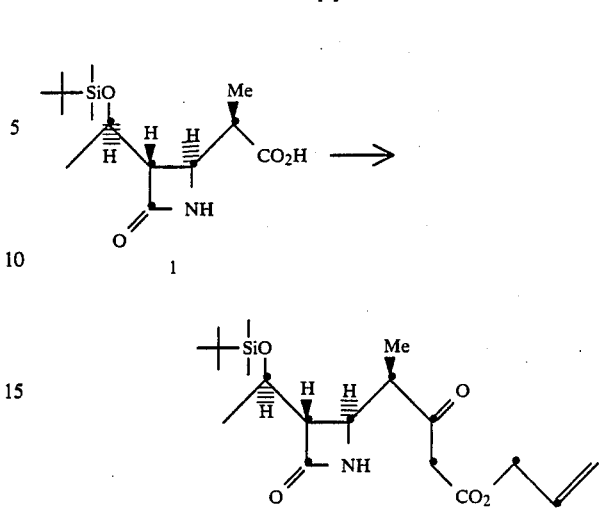

Step 1: Preparation of (3S,4R)-3-[(R)-1-t-butyldimethylsilyloxyethyl]-4-[(R)-1-methyl-3-allyloxycarbonyl-2-oxopropyl]-2-azetidinone (2)

A solution of carboxylic acid 1 (1.68 g, 5.57 mmol) in anhyd. acetonitrile (50 ml) was treated with carbonyl diimidazole (1.08 g, 6.68 mmol, 1.2 eg) and stirred 1 hour at room temperature. Magnesium allyl malonate (1.73 g, 5.57 mmol) was added and the mixture was stirred and heated in an oil bath at 60° for 12 hours. The mixture was evaporated under vacuum. The residue was taken up in ethylacetate, washed with 1N HCl, water, 10% K₂CO₃, water and brine, dried with magnesium sulfate, filtered, and evaporated under vacuum to give a pale yellow oil (1.62 g). This material was chromatographed on EM silica gel 60 (40 g) using 2:1 methylene chloride-ethyl acetate as eluting solvent; 15 ml fractions were collected every 2 minutes. Fractions 7–11 were combined and evaporated under vacuum to provide compound 2 (1.135 g) as a white solid.

Step 2: Preparation of (3S,4R)-3-[(R)-1-hydroxyethyl]-4-[(R)-1-methyl-3-allyloxycarbonyl-2-oxopropyl]-2-azetidinone (3)

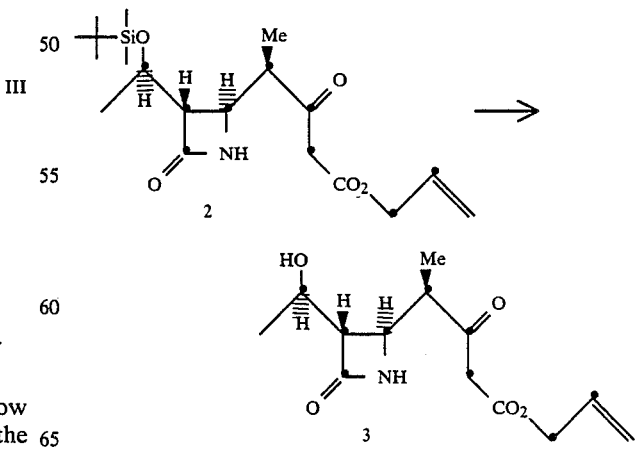

The keto ester 2 (1.047 g, 2.73 mmol) in methanol (12.3 ml) was treated with 6N HCl (1.37 ml, 8.22 mmol, 3 eg) and stirred 1 hour at room temperature. The solution was treated with 1M K₂HPO₄ (8.2 ml) and stirred a few minutes, then diluted with ethylacetate and water. The organic layer was separated, washed with 5% NaHCO₃ and brine, dried with magnesium sulfate, filtered, and evaporated under vacuum to give the product 3 (0.653 g, 89%) as a clear oil.

Step 3: Preparation of (3S,4R)-3-[(R)-1-hydroxyethyl]-4-[(R)-1-methyl-3-diazo-3-allyloxycarbonyl-2-oxopropyl]-2-azetidinone (4)

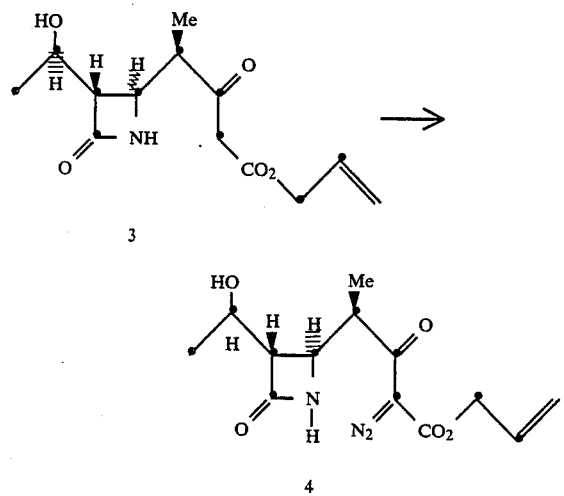

A solution of β-keto ester 3 (0.65 g, 2.41 mmol) in anhydrous acetonitrile (9.6 ml) was treated with triethylamine (0.40 ml, 2.89 mmol) and a solution of p-dodecylbenzenesulfonyl azide in hexane (3.3 ml of a 0.87M solution, 2.89 mmol). The resulting solution was stirred at room temperature in a capped flask for 1 hour, then evaporated under vacuum. The residue was taken up in ethyl acetate, washed with water (2×) and brine, dried with magnesium sulfate, filtered and evaporated under vacuum to give a yellow oil (1.765 g). The crude product was chromatographed on EM silica gel 60 (35 g) using 1:2 methylene chloride ethylacetate as eluant; 25 ml fractions were collected every 3 minutes. Fractions 8–20 gave the crude diazo keto ester 4 (67%, 0.48 g) as a pale yellow oil. The product partially solidified on storing in a freezer. The mixture was triturated with petroleum ether-diethyl ether and the solid portion collected, washed with additional petroleum ether-diethyl ether and dried under vacuum to give 4 as white crystals.

Step 4: Preparation of Allyl (1R,3R,5R,6S)-6-[(R)-1-hydroxyethyl]-1-methyl-2-oxocarbapenam-3-carboxylate (5)

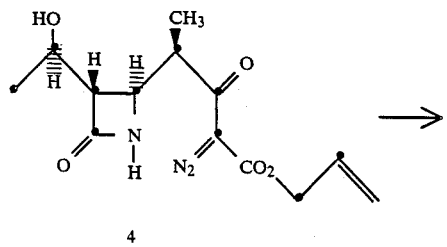

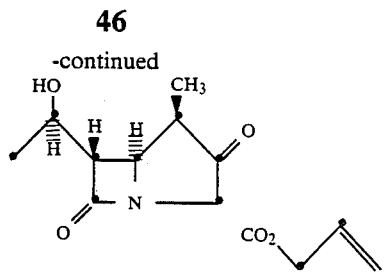

A mixture of crystalline diazo keto ester 4 (45 mg, 0.152 mmol) rhodium octanoate (1.2 mg, 0.00154 mmol) and anhydrous toluene (3.0 ml) was heated in an oil bath at 80° and under a nitrogen atmosphere for 15 minutes. (Note: gas evolution occurred at room temperature before heating). After cooling to room temperature, the reaction mixture was diluted with ethyl acetate (3 ml), dried over magnesium sulfate, filtered, evaporated under vacuum and stripped with methylene chloride to afford 5 as a pale green oil (41 mg, 100%).

Spectral data for 5:
IR(CH₂Cl₂) 3600, 1765, 1745, 1210 cm⁻¹;
NMR(CDCl₃) δ 1.22(d, J=7.8 Hz, CH₃CH), 1.39(d, J=6.2 Hz, CH₃CHOH), 2.85(dq, J=7.8 Hz, CH₃CH), 3.27(dd, J=2.3 and 6.9 Hz, H6), 4.27(dd, J=2.3 and 7.8 Hz, H5), 4.33(m, CH₃CHOH), 4.70(m, H3 and OCH₂), 5.35(m, =CH₂), 5.90(m, CH=);
MS (Mass Spectrum) m/e 267 (M+), 249, 226, 223, 182, 164, 138.

EXAMPLE 24

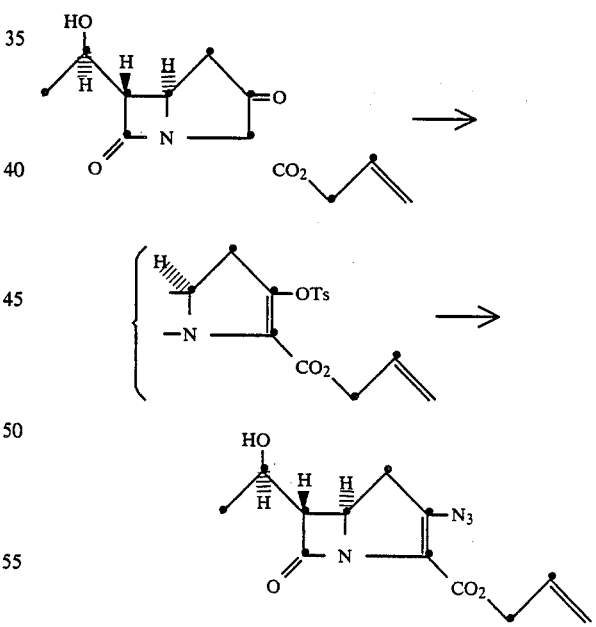

Preparation of Allyl (5R,6S)-2-Azido-6-[(R)-1-hydroxyethyl]carbapen-2-em-3-carboxylate (28)

A solution of allyl (3R,5R,6S)-6-[(R)-1-hydroxyethyl]-2-oxo-carbapenem-3-carboxylate (25.3 mg, 0.1 mmol), prepared by the preceding Example 24A, in anhydrous methylene chloride (1.0 ml) was treated with p-toluenesulfonic anhydride (32.6 mg, 0.1 mmol) and N,N-diisopropylethylamine (19.2 μl, 0.11 mmol), and the resulting solution was stirred at 0° and under a nitrogen atmosphere for 3 hours. The solution was diluted with methylene chloride, washed with water, 5% aqueous sodium bicarbonate and brine, dried with magnesium sulfate, and evaporated under vacuum. The residue was chromatographed on a 0.5 mm×20×20 cm silica gel GF plate using 1:1 ethyl acetate-methylene chloride as developing solvent to provide allyl (5R,6S)-6-[(R)-1-hydroxyethyl]-2-(p-toluenesulfonyloxy)carbapen-2-em-3-carboxylate (12 mg) as a clear oil.

The tosylate (12 mg, 0.029 mmol) in anhydrous methylene chloride (0.03 ml) and anhydrous acetonitrile (0.12 ml) was cooled to 0° C., treated with 1,4,7,10,13,16-hexaoxacyclooctadecane (7.7 mg, 0.029 mmol) and sodium azide (5.7 mg, 0.088 mmol), and stirred in the cold for 100 minutes. The mixture was diluted with ethyl acetate, washed with water, dried with magnesium sulfate, filtered, and evaporated under vacuum to an oil (8.5 mg). The residue was purified by preparative layer chromatography on a 0.25 mm×8.5×20 cm silica gel GF plate using 3:1 methylene choride-ethyl acetate as developing solvent to afford allyl (5R,6S)-2-azido-6-[(R)-1-hydroxyethyl]carbapen-2-em-3-carboxylate (1.2 mg) as a clear oil: IR (neat) 2115, 1770, 1745, 1700, 1590 cm$^{-1}$;

NMR (CDCl$_3$) δ 1.36 (d, J=6.2 Hz, CH$_3$CH), 3.11 (d, J=9.6 Hz, CH$_2$), 3.21 (dd, J=2.7 and 7.1 Hz, H6), 4.24 (m, H5 and CH$_3$CH).

EXAMPLE 25

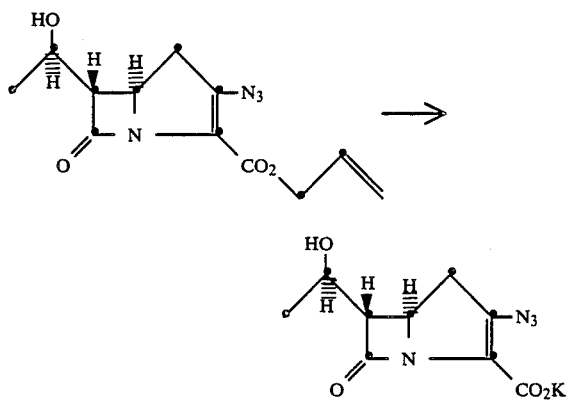

Preparation of Potassium (5R,6S)-2-Azido-6-[(R)-1-hydroxyethyl]carbapen-2-em-3-carboxylate (29)

A solution of allyl (5R,6S)-2-azido-6-[(R)-1-hydroxyethyl]carbapen-2-em-3-carboxylate (42 mg, 0.15 mmol) and triphenylphosphine (12 mg, 0.045 mmol) in 1:1 methylene chloride-ethyl acetate (2.7 ml) is treated with 0.5M potassium 2-ethylhexanoate in ethyl acetate (0.3 ml, 0.15 mmol) and tetrakis(triphenylphosphine)-palladium (O) (13.8 mg, 0.012 mmol). The mixture is stirred 15 minutes at ambient temperature under a nitrogen atmosphere, diluted with diethyl ether, and centrifuged. The insoluble pellet is washed with ether and dried under vacuum to afford potassium (5R,6S)-2-azido-6-[(R)-1-hydroxyethyl]carbapen-2-em-3-carboxylate.

EXAMPLE 26

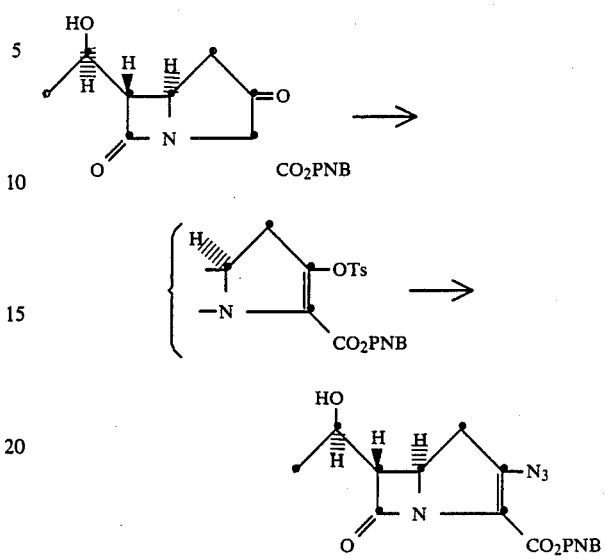

Preparation of p-Nitrobenzyl (5R,6S)-2-azido-6-[(R)-1-hydroxyethyl]carbapen-2-em-3-carboxylate (30)

A solution of p-nitrobenzyl (3R,5R,6S)-6[(R)-1-hydroxyethyl]-2-oxocarbapenam-3-carboxylate (348 mg, 1 mmol) in anhydrous acetonitrile (10 ml) is cooled to 0° C. under a nitrogen atmosphere and treated with N,N-diisopropylethylamine (192 μl, 1.1 mmol) and freshly recrystallized p-toluenesulfonic anhydride (343 mg, 1.05 mmol). The resulting solution is stirred at 0° C. for 1 hour to provide p-nitrobenzyl (5R,6S)-6-[(R)-1-hydroxyethyl]-2-(p-toluenesulfonyloxy)carbapen-2-em-3-carboxylate.

The solution is treated with potassium azide (243 mg, 3 mmol) and with a solution of 1,4,7,10,13, 16-hexaoxacyclooctadecane (264 mg, 1 mmol) in anhydrous methylene chloride (1 ml). The resulting mixture is stirred at 0° C. for 3 hours, then filtered through a small pad of florisil which is washed with ethyl acetate. The filtrate and wash are evaporated under vacuum to a residue which is purified by preparative layer chromatography on silica gel to afford p-nitrobenzyl (5R,6S)-2-azido-6-[(R)-1-hydroxyethyl]carbapen-2-em-3-carboxylate.

EXAMPLE 27

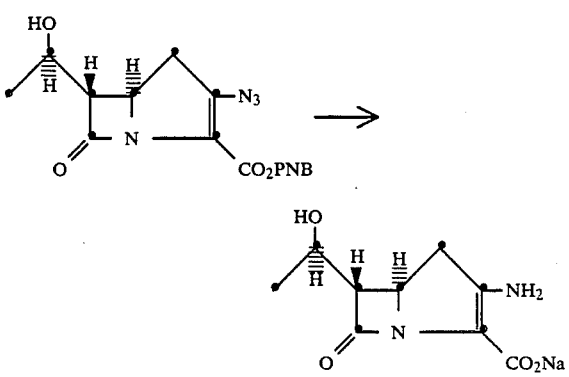

Preparation of Sodium
(5R,6S)-2-amino-6-[(R)-1-hydroxyethyl]carbapen-2-em-3-carboxylate (31)

A mixture of p-nitrobenzyl (5R,6S)-2-azido-6-[(R)-1-hydroxyethyl]carbapen-2-em-3-carboxylate (75 mg, 0.2 mmol), tetrahydrofuran (14 ml), ethanol (14 ml), deionized water (11 ml) containing sodium bicarbonate (16.8 mg, 0.2 mmol), and 10% palladium on carbon (75 mg) is shaken under hydrogen (45 psi) at ambient temperature for 2 hours. The mixture is filtered through a celite pad to remove the catalyst which is washed with water. The combined filtrate and wash is extracted with three portions of diethyl ether, concentrated under vacuum to about 10 ml volume, and lyophilized to afford sodium (5R,6S)-2-amino-6-[(R)-1-hydroxyethyl]carbapen-2-em-3-carboxylate.

EXAMPLE 28

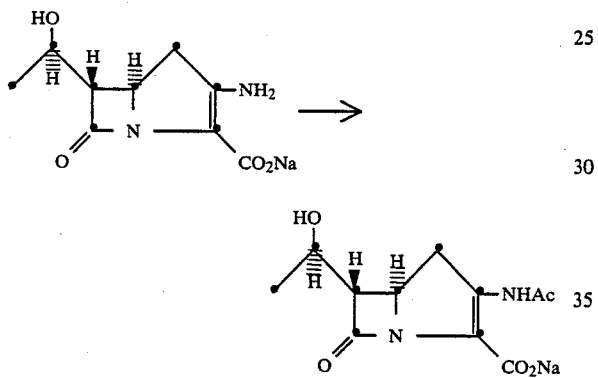

Preparation of Sodium
(5R,6S)-2-acetamido-6-[(R)-1-hydroxyethyl]carbapen-2-em-3-carboxylate (32)

A solution of sodium (5R,6S)-2-amino-6-[(R)-1-hydroxyethyl]carbapen-2-em-3-carboxylate (23 mg, 0.1 mmol) in water (2.5 ml) is cooled in an ice-bath, stirred, and treated with sodium bicarbonate (84 mg, 1 mmol) and dioxane. The resulting solution is stirred in the cold while a solution of acetyl chloride (11 μl, 0.15 mmol) in dioxane (0.5 ml) is added dropwise over 10 minutes. After stirring an additional 30 minutes, the solution is acidified to pH 6.8 with 1M sulfuric acid and extracted with diethyl ether (3×10 ml). The aqueous phase is layered with ethyl acetate (2.5 ml) and vigorously stirred in an ice-bath while acidifying to pH 2.3 with 1M sulfuric acid. The aqueous phase is separated and extracted with more ethyl acetate (2×2 ml). The combined ethyl acetate solution is washed with brine, then layered with water (5 ml) and stirred vigorously in an ice-bath while the pH is brought to 7 with 1N sodium hydroxide. The aqueous phase is separated, concentrated under vacuum, and lyophilized to yield sodium (5R,6S)-2-acetamido-6-[(R)-1-hydroxyethyl]carbapen-2-em-3-carboxylate (32).

EXAMPLE 29

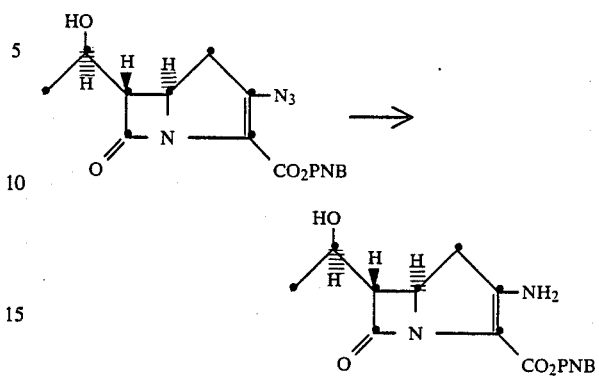

Preparation of p-Nitrobenzyl
(5R,6S)-2-amino-6-[(R)-1-hydroxyethyl]carbapen-2-em-3-carboxylate (33)

A solution of p-nitrobenzyl (5R,6S)-2-azido-6-[(R)-1-hydroxyethyl]carbapen-2-em-3-carboxylate (37 mg, 0.1 mmol) and triethylamine (14 μl, 0.1 mmol) in anhydrous tetrahydrofuran (2 ml) is cooled in an ice-bath while hydrogen sulfide is gently bubbled in over 15 minutes. After an additional 15 minutes at 0°, the solution is evaporated under vacuum and the residue is purified by preparative layer chromatography on silica gel to afford p-nitrobenzyl (5R,6S)-2-amino-6-[(R)-1-hydroxyethyl]carbapen-2-em-3-carboxylate.

EXAMPLE 30

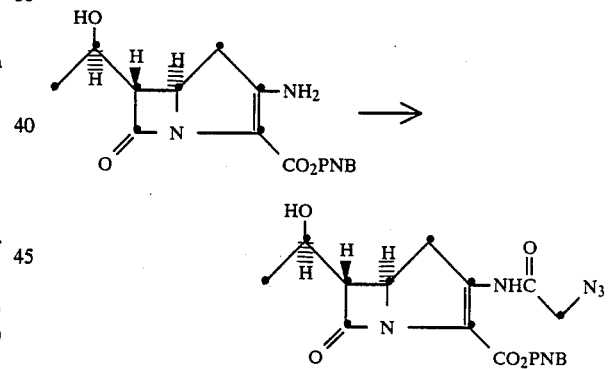

Preparation of p-Nitrobenzyl
(5R,6S)-2-(2-azidoacetamido)-6-[(R)-1-hydroxyethyl]-carbapen-2-em-3-carboxylate (34)

A solution of p-nitrobenzyl (5R,6S)-2-amino-6-[(R)-1-hydroxyethyl]carbapen-2-em-3-carboxylate (35 mg, 0.1 mmol) in anhydrous tetrahydrofuran (2 ml) is cooled to −25° C. and treated with 4-dimethylamino pyridine (15.9 mg, 0.13 mmol) and, dropwise over 5 minutes, with a solution of 2-azidoacetyl chloride (14.3 mg, 0.12 mmol) in tetrahydrofuran (0.5 ml). The resulting mixture is stirred under a nitrogen atmosphere at 0° C. for 4 hours. The mixture is diluted with ethyl acetate, washed with pH 3 phosphate buffer, water, 5% aqueous sodium bicarbonate and brine, dried over magnesium sulfate, filtered, and evaporated under vacuum. The residue is chromatographed on a silica gel thin layer preparative plate to afford the title compound.

EXAMPLE 31

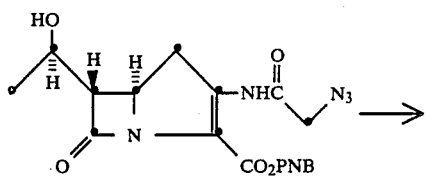

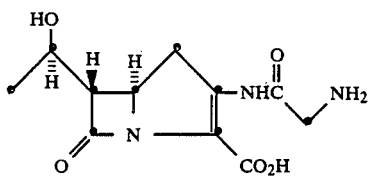

Preparation of (5R,6S)-2-(2-Aminoacetamido)-6-[(R)-1-hydroxyethyl]-carbapen-2-em-3-carboxylic acid (35)

A solution of p-nitrobenzyl (5R,6S)-2-(2-azidoacetamide)-6-[(R)-1-hydroxyethyl]carbapen-2-em-3-carboxylate (10.8 mg, 0.025 mmol) in N,N-dimethylacetamide (0.2 ml) is diluted with n-butanol (1.0 ml), ethyl acetate (0.5 ml), water (1.0 ml), and 0.5M pH 6.8 N-methylmorpholinehydrochloric acid buffer (0.5 ml). The resulting mixture is treated with 20% palladium hydroxide on carbon (10 mg) and hydrogenated on a Parr apparatus at 45 psi for 2 hours at ambient temperature. The mixture is filtered through a celite pad which is washed with water. The aqueous portion of the combined filtrate and wash is extracted twice with methylene chloride and once with diethyl ether. The aqueous phase is concentrated under vacuum to about 2 ml volume and added to a column of Dowex 50W×4 resin (sodium form, 200-400 mesh) which is eluted with DI water in a cold room. The appropriate fractions, as identified by UV monitoring, are combined, concentrated under vacuum, and lyophilized to provide (5R,6S)-2-(2-aminoacetamido)-6-[(R)-1-hydroxyethyl]-carbapen-2-em-3-carboxylic acid.

EXAMPLE 32

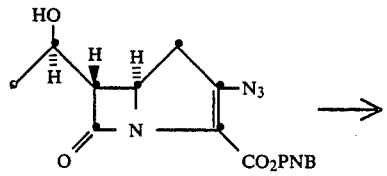

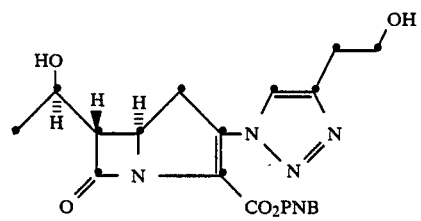

Preparation of p-Nitrobenzyl (5R,6S)-6-[(R)-1hydroxyethyl]-2-[4-(2-hydroxyethyl)-1,2,3-triazol-1-yl]carbapen-2-em-3-carboxylate (36)

A mixture of p-nitrobenzyl (5R,6S)-2-azido-6-[(R)-1-hydroxyethyl]-carbapen-2-em-3-carboxylate (75 mg, 0.2 mmol) and 2,3-dihydrofuran (0.25 ml) in anhydrous tetrahydrofuran (5 ml) containing excess sodium bicarbonate is kept at 4° C. for 1 week. The mixture is filtered and the filtrate evaporated under vacuum. The residue is purified by preparative thin layer chromatography on silica gel to afford p-nitrobenzyl (5R,6S)-6-[(R)-1-hydroxyethyl]-2-[4-(2-hydroxyethyl)-1,2,3-triazol-1-yl]carbapen-2-em-3-carboxylate.

EXAMPLE 33

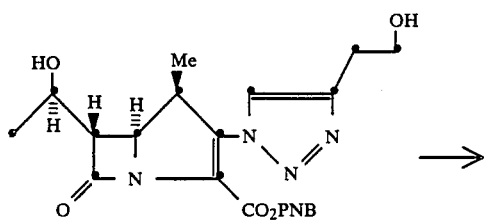

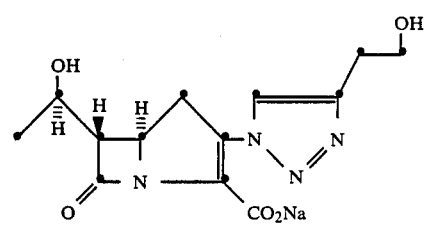

Preparation of Sodium (5R,6S)-6-[(R)-1-hydroxyethyl]-[4-(2-hydroxyethyl)-1,2,3-triazol-1-yl]carbapen-2-em-3-carboxylate (37)

A solution of p-nitrobenzyl (5R,6S)-6-[(R)-1-hydroxyethyl]-2-[4-(2-hydroxyethyl)-1,2,3- triazol-1-yl]carbapen-2-em-3-carboxylate (35 mg, 0.08 mmol) in tetrahydrofuran (5.5 ml) is diluted with ethanol (2.8 ml) and DI water (4.2 ml) containing sodium bicarbonate (6.8 mg, 0.08 mmol). The resulting solution is added to a prereduced mixture of 10% palladium on carbon (37 mg) in ethanol (2.7 ml), and the mixture is stirred under an atmosphere of hydrogen for 2 hours at ambient temperature. The mixture is filtered through a celite pad which is washed with water. The filtrate and wash are extracted with methylene chloride and diethyl ether, concentrated under vacuum, and lyophilized to afford sodium (5R,6S)-6-[(R)-1-hydroxyethyl]-2-[4-(2-hydroxyethyl)-1,2,3-triazol-1-yl]carbapen-2-em-3-carboxylate.

EXAMPLE 34

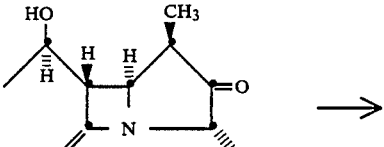

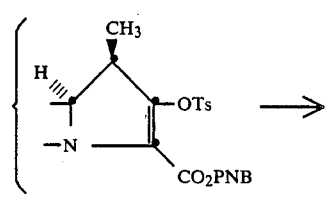

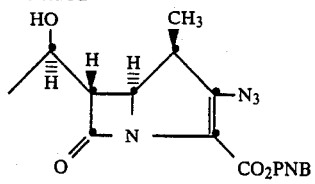

Preparation of p-Nitrobenzyl (1R,5R,6S)-2-azido-6-[(R)-1-hydroxyethyl]-1-methyl-carbapen-2-em-3-carboxylate (38)

A solution of p-nitrobenzyl (1R,3R,5R,6S)-6-[(R)-1-hydroxyethyl]-2-oxo-1-methylcarbapenam-3-carboxylate (362 mg, 1 mmol) prepared by the method of D. H. Shih, et al., *Heterocycles*, 21(1), pp. 29–40 (1984), hereby incorporated by reference for this particular purpose, in anhydrous acetonitrile (10 ml) is cooled to 0° C. and treated with N,N-diisopropylethylamine (192 μl, 1.1. mmol) and p-toluenesulfonic anhydride (343 mg, 1.09 mmol). The resulting solution is stirred at 0° C. under a nitrogen atmosphere for one hour to provide p-nitrobenzyl (1R,5R,6S)-6-[(R)-1-hydroxyethyl]-2-(p-toluenesulfonyloxy)-1-methylcarbapen-2-em-3-carboxylate.

The solution of the bicyclic tosylate is treated with potassium azide (243 mg, 3 mmol) and with a solution of 1,4,7,10,13,16-hexaoxacyclooctadecane (264 mg, 1 mmol) in methylene chloride (1 ml). The resulting mixture is stirred at 0° C. for 5 hours, then filtered through a small column of florisil which was eluted with ethyl acetate. The filtrate and wash are evaporated under a vacuum to a residue which is purified by flash chromatography on silica gel to afford the title compound.

EXAMPLE 35

By employing procedures analogous to those described in Examples 1–34, the following compounds are prepared:

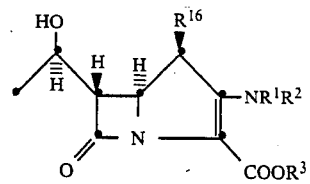

| Compound | $R^{16}$ | $NR^1R^2$ | $R^3$ |
|---|---|---|---|
| 39 | H | 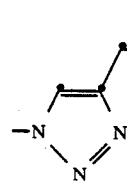 | Na |
| 40 | H | 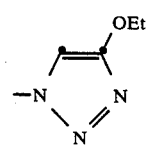 | Na |
| 41 | H | (EtO-substituted triazole) | Na |
| 42 | H | ($Et_2N$, $CH_3$-substituted triazole) | H |
| 43 | H | ($CH_3$-substituted triazole) | Na |
| 44 | H | ($H_3C$-substituted triazole) | Na |
| 45 | H | $-N(CH_3)(CH_2OCCH_3)$ with C=O | Na |
| 46 | H | $-N$ (aziridine with $CO_2CH_2CH_3$) | Na |
| 47 | H | $-NHSO_2$—C$_6$H$_4$—CH$_3$ | Na |
| 48 | H | $-NHSO_2CH_3$ | Na |
| 49 | H | $-NHC(O)NHCH_3$ | Na |
| 50 | H | $-NHC(O)N(CH_3)_2$ | Na |
| 51 | H | $-NHC(O)CH_2$—C$_6$H$_5$ | Na |

-continued
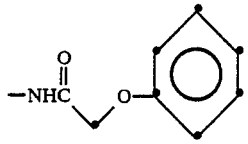
| Compound | R16 | NR1R2 | R3 |
|---|---|---|---|
| 52 | H | 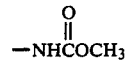 | Na |
| 53 | H | 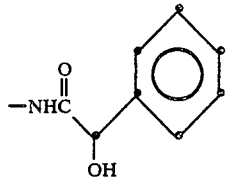 | Na |
| 54 | H |  | Na |
| 55 | H | 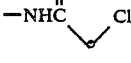 | Na |
| 56 | H |  | Na |
| 57 | H | 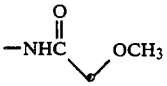 | Na |
| 58 | H | 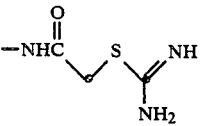 | Na |
| 59 | H | 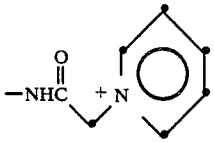 | H |
| 60 | H | 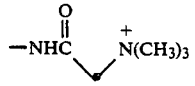 | (−) |
| 61 | H | 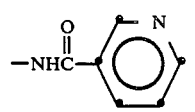 | (−) |
| 62 | H | 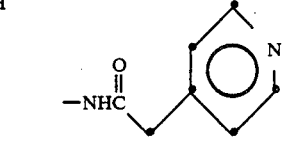 | Na |
-continued
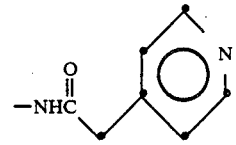
| Compound | R16 | NR1R2 | R3 |
|---|---|---|---|
| 63 | H |  | Na |
| 64 | H | 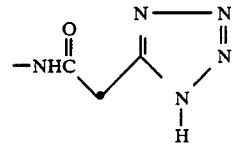 | Na |
| 65 | H | 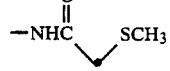 | Na |
| 66 | H | 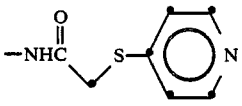 | Na |
| 67 | H | 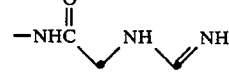 | Na |
| 68 | H | 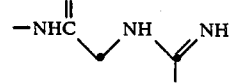 | H |
| 69 | H | 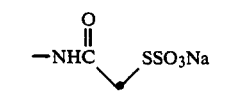 | H |
| 70 | H |  | Na |
| 71 | H |  | Na |
| 72 | H |  | H |
| 73 | H | | H |

-continued

| Compound | R16 | NR1R2 | R3 |
|---|---|---|---|
| 74 | H | —NHC(=S)—C6H5 | Na |
| 75 | H | —NHC(=O)S—C6H5 | Na |
| 76 | H | —NHS(=O)2—C6H5 | Na |
| 77 | H | —NHP(=S)(OCH3)2 | Na |
| 78 | H | —NHP(=O)(OCH3)2 | Na |
| 79 | H | —NHP(=S)(OCH3)(ONa) | Na |
| 80 | H | —NHP(=O)(OCH3)(ONa) | Na |
| 81 | H | —NHP(=O)(N(CH3)2)2 | Na |
| 82 | H | —NHS(=O)2NH2 | Na |
| 83 | H | —NHC(=S)NH2 | Na |
| 84 | H | —NHC(=O)CH2—S—CH2CN | Na |
| 85 | H | —NHC(=O)CH2—S—CH2-(2-pyridyl) | Na |
| 86 | H | —NHC(=O)CH2—S—CH2-(N-methylpyridinium) | (−) |
| 87 | H | —NHCH3 | Na |
| 88 | H | —N(CH3)2 | Na |
| 89 | H | —N(CH3)C(=O)CH3 | Na |
| 90 | H | —N-(2-oxopyrrolidinyl) | Na |
| 91 | H | —N-(phthalimido) | Na |
| 92 | H | —NHC(=O)CH2-(pyridyl) | Na |
| 93 | H | —NHC(=O)CH2-(N-methylpyridinium) | (−) |
| 94 | H | —N-(3-methyl-2-oxoimidazolidinyl) | Na |
| 95 | H | —N-(2-oxooxazolidinyl) | Na |
| 96 | CH3 | —N3 | Na |
| 97 | CH3 | —NH2 | Na |

-continued $$\text{HO} \underset{\overline{H}}{\overset{R^{16}}{\diagdown}} \underset{H}{\overset{H}{\diagdown}} \text{NR}^1\text{R}^2$$
(structure with β-lactam ring, COOR³)

| Compound | R¹⁶ | NR¹R² | R³ |
|---|---|---|---|
| 98 | CH₃ | —NHC(O)CH₃ | Na |
| 99 | CH₃ | —NHC(O)NHCH₃ | Na |
| 100 | CH₃ | —NHC(O)H | Na |
| 101 | CH₃ | —NHC(O)CH₂Cl | Na |
| 102 | CH₃ | —NHC(O)CH₂N₃ | Na |
| 103 | CH₃ | —NHC(O)CH₂NH₂ | H |
| 104 | CH₃ | —NHC(O)CH₂OCH₃ | Na |
| 105 | CH₃ | —NHC(S)O—C₆H₅ | Na |
| 106 | CH₃ | —NHC(O)CH₂S—C(NH)NH₂ | H |
| 107 | CH₃ | —NHC(O)CH₂N₃ | Na |
| 108 | CH₃ | —NHC(O)CH₂NH₂ | H |
| 109 | CH₃ | —NHC(O)CH₂S-pyridyl | Na |
| 110 | CH₃ | —NHC(S)NH₂ | Na |
| 111 | CH₃ | —NHCH₃ | Na |
| 112 | CH₃ | —N(CH₃)₂ | Na |

-continued $$\text{HO} \underset{\overline{H}}{\overset{R^{16}}{\diagdown}} \underset{H}{\overset{H}{\diagdown}} \text{NR}^1\text{R}^2$$
(structure with β-lactam ring, COOR³)

| Compound | R¹⁶ | NR¹R² | R³ |
|---|---|---|---|
| 113 | CH₃ | —N(CH₃)—C(O)CH₃ | Na |
| 114 | CH₃ | —N(pyrrolidinone) | Na |
| 115 | CH₃ | —N(phthalimide) | Na |
| 116 | CH₃ | —N(triazole-CH₂CH₂OH) | Na |

EXAMPLE 36

Preparation of Pharmaceutical Compositions

One such unit dosage form is prepared by mixing 120 mg of compound A (compound of Example 28) with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as compressed tablets and pills can be prepared. The following examples are illustrative of the preparation of pharmaceutical formulations:

| TABLET | PER TABLET |
|---|---|
| Compound A | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| PARENTERAL SOLUTION | PER TABLET |
|---|---|
| Ampoule: | |
| Compound A | 500 mg. |
| Diluent: Sterile Water for Injection | 2 cc. |
| OPHTHALMIC SOLUTION | |
| Compound A | 100 mg. |
| Hydropropylmethyl Cellulose | 5 mg. |
| Sterile Water | to 1 ml. |
| OTIC SOLUTION | |
| Compound A | 100 mg. |
| Benzalkonium chloride | 0.1 mg. |
| Sterile Water | to 1 ml. |
| TOPICAL OINTMENT | |
| Compound A | 100 mg. |
| Polyethylene Glycol 4000 U.S.P. | 400 mg. |
| Polyethylene Glycol 400 U.S.P. | 1.0 gram |

What is claimed is:

1. A compound of the formula:

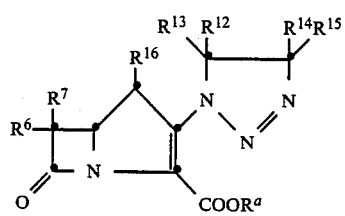

wherein $R^{16}$ is H or methyl; $R^7$ and $R^6$ are chosen from hydrogen, linear, branched or cyclic $C_1$-$C_5$ alkyl, which can be substituted with fluoro, hydroxy, protected hydroxy; sulfoxy, amino, protected amino, wherein $R^6$ and $R^7$ taken together can also be $C_2$-$C_4$ alkylidene, optionally substituted by the above substituents with the proviso that both $R^6$ and $R^7$ are not unsubstituted alkyl, and $R^a$ is hydrogen, or pharmaceutically acceptable salt cation or ester group; wherein $R^{12}$, $R^{13}$, $R^{14}$ and $R^{15}$ are independently chosen from H, alkyl, which can be substituted with OH, alkoxyl, acyloxy, amino, mono- and dialkylamino, or $NR^{11}C(X)R^{11}$; and wherein $R^{12}$, $R^{13}$, $R^{14}$, and $R^{15}$, can also be phenyl, benzyl, pyridyl, pyridylmethyl, thienyl, or thienylmethyl which can be substituted with up to 2 or halo, $OR^{11}$, $NR_2^{11}$, $OCO^{11}$, or $NR^{11}C(X)R^{11}$; and further wherein $R^{12}$ and $R^{14}$ can be joined to form a cis-fused ring of 5 or 6 atoms containing up to 2 heteroatoms, selected from O, N, S, SO, or $SO_2$.

2. The compound of claim 1 wherein $R^{13}$ and $R^{15}$ are H, and $R^{12}/R^{14}$ are cis-fused $-CH_2CH_2O-$ or $CH_2CH_2CH_2O-$.

3. The compound of claim 1 wherein $R^7$ is hydrogen and $R^6$ is selected from H, $CH_3CH_2-$, $(CH_3)_2CH-$, $HOCH_2-$, $CH_3CHOH-$, $(CH_3)_2COH-$, $FCH_2CHOH-$, $CH_3CHF-$, $CH_3CF_2-$, $CH_3CHOSO_3H-$, $(CH_2)_2COH-$, or $CH_3CHNH_2-$; or $R^6$ and $R^7$ together are $CH_3C(CH_2OH)=$.

4. The compound of claim 1 of the configurational structure:

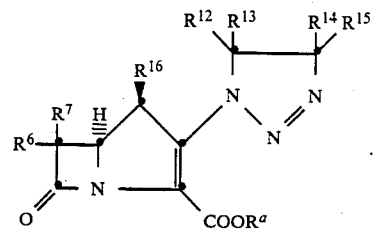

5. The compound of claim 4 of the formula:

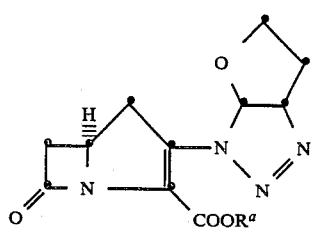

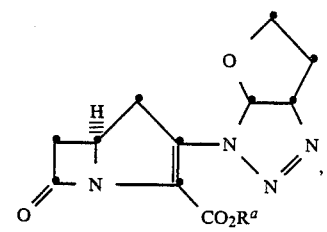

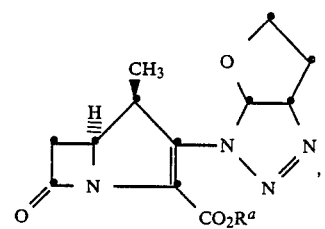

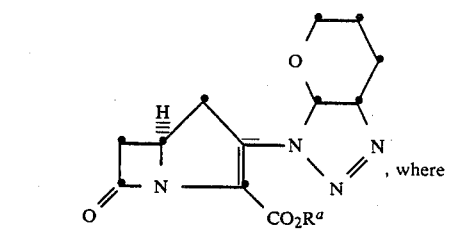, where $R^a$ is benzyl, p-nitrobenzyl, allyl, sodium, potassium or hydrogen.

6. A process for preparing the compound of claim 1 comprising the step of contacting the azide of the formula:

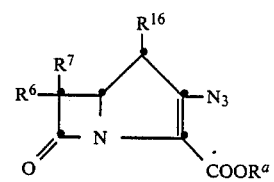

wherein $R^6$, $R^7$, $R^{16}$ and $R^a$ are defined in claim 1, with an alkene of the formula:

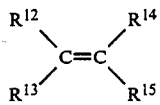

under liquid reaction conditions at −40° to 100° C. for a sufficient time to produce

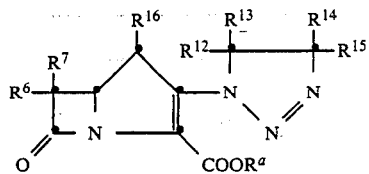

7. A pharmaceutical composition for antibiotic use comprising an antibacterially effective amount of a compound of claim 1, and optionally, a pharmaceutically acceptable carrier.

8. A method of treating bacterial infections in human or animal subjects in need of such treatment comprising administering to said subjects an antibacterially effective amount of a compound of claim 1.

* * * * *